(12) United States Patent
Carr et al.

(10) Patent No.: US 11,202,708 B2
(45) Date of Patent: Dec. 21, 2021

(54) SEGMENTED, GROWTH-ACCOMMODATING, ARTIFICIAL VALVE

(71) Applicant: THE CHARLES STARK DRAPER LABORATORY, INC., Cambridge, MA (US)

(72) Inventors: Jesse M. Carr, Cambridge, MA (US); Corin Williams, Framingham, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 71 days.

(21) Appl. No.: 16/179,482

(22) Filed: Nov. 2, 2018

(65) Prior Publication Data

US 2019/0133764 A1    May 9, 2019

Related U.S. Application Data

(60) Provisional application No. 62/583,049, filed on Nov. 8, 2017.

(51) Int. Cl.
*A61F 2/24* (2006.01)

(52) U.S. Cl.
CPC .......... *A61F 2/2445* (2013.01); *A61F 2/2409* (2013.01); *A61F 2/2412* (2013.01); *A61F 2/2418* (2013.01); *A61F 2250/001* (2013.01); *A61F 2250/0082* (2013.01)

(58) Field of Classification Search
CPC ....................................................... A61F 2/24
See application file for complete search history.

(56) References Cited

U.S. PATENT DOCUMENTS

| 4,192,020 A * | 3/1980 | Davis ..................... D03D 15/00 623/2.19 |
| 4,473,423 A * | 9/1984 | Kolff ..................... A61F 2/2409 156/245 |
| 5,411,552 A * | 5/1995 | Andersen .............. A61F 2/2418 137/343 |
| 2007/0260305 A1 * | 11/2007 | Drews ................... A61F 2/2427 623/2.11 |

(Continued)

FOREIGN PATENT DOCUMENTS

| EP | 1765225 B1 | 9/2015 |
| WO | 2006005015 A3 | 4/2006 |
| WO | 2012094474 A1 | 7/2012 |

OTHER PUBLICATIONS

International Search Report and the Written Opinion of the International Searching Authority from corresponding PCT/US2018/059281 dated Feb. 20, 2019.

*Primary Examiner* — Jacqueline Woznicki
(74) *Attorney, Agent, or Firm* — Lando & Anastasi, LLP

(57) ABSTRACT

According to various aspects and embodiments, a prosthetic valve assembly for controlling fluid flow in an annulus is provided. The prosthetic valve assembly includes a suture ring formed from two or more segments, where each segment is configured to attach to the annulus, and a leaflet subassembly that attaches to an inner portion of at least one segment of the suture ring. The leaflet subassembly includes at least one leaflet configured for controlling a flow of fluid through the prosthetic valve assembly.

28 Claims, 19 Drawing Sheets

(56) References Cited

U.S. PATENT DOCUMENTS

| | | |
|---|---|---|
| 2010/0076548 A1 | 3/2010 | Konno |
| 2013/0018458 A1* | 1/2013 | Yohanan ............... A61F 2/2418 623/2.18 |
| 2014/0188219 A1* | 7/2014 | Conklin ............... A61F 2/2445 623/2.17 |
| 2016/0045312 A1* | 2/2016 | Braido ...................... A61F 2/24 623/2.37 |
| 2017/0065408 A1* | 3/2017 | Grundeman .......... A61F 2/2418 |
| 2019/0209319 A1* | 7/2019 | Konno ................. A61F 2/2412 |

\* cited by examiner

SEGMENTED, GROWTH-ACCOMMODATING, ARTIFICIAL VALVE

CROSS-REFERENCE TO RELATED APPLICATION

This application claims priority under 35 U.S.C. § 119(e) to U.S. Provisional Application Ser. No. 62/583,049 titled "SEGMENTED, GROWTH-ACCOMMODATING, ARTIFICIAL VALVE" filed Nov. 8, 2017, which is incorporated herein by reference in its entirety for all purposes.

BACKGROUND

Prosthetic valve devices are typically constructed with geometries and configurations that are not designed to grow with the patient. In addition, adult-sized replacement heart valves typically have large-scale fixed features that require doctors to significantly modify the device for purposes of accommodating a pediatric patient. Few physicians perform this difficult and complicated procedure. Furthermore, successive invasive procedures are necessary later in the patient's life since the device does not grow with the child.

SUMMARY

Aspects and embodiments are directed to a prosthetic valve assembly for controlling fluid flow in an annulus.

According to one embodiment, the prosthetic valve assembly includes a suture ring formed from two or more segments, each segment of the two or more segments having an outer portion configured for attachment to the annulus, and a leaflet subassembly attached to an inner portion of at least one segment of the suture ring, the leaflet subassembly including at least one leaflet configured for controlling a flow of fluid through the prosthetic valve assembly.

In one example, the at least one leaflet includes an outer edge configured to attach to the inner portion of the at least one segment.

In one example, the at least one leaflet and the at least one segment form a continuous structure.

In one example, the leaflet subassembly further includes a spring rib coupled to the at least one leaflet. In another example, a portion of the spring rib is attached to the inner portion of the at least one segment.

In one example, a surface of the at least one leaflet has a plurality of expansion elements. In one example, the plurality of expansion elements are pleats.

In one example, the valve assembly further includes a shielding structure attached to the suture ring and configured to extend laterally between the at least one leaflet and the annulus, the shielding structure defined by a plurality of shielding segments.

In one example, the leaflet subassembly includes a sinus structure.

In one example, the shielding segments are more rigid than the at least one leaflet.

In another example, at least a portion of each shielding segment of the plurality of shielding segments is attached to a segment of the suture ring.

In one example, the suture ring, the at least one leaflet, and the shielding structure form a continuous structure.

In one example, a portion of a shielding segment of the plurality of shielding segments is coupled to an adjacent shielding segment of the plurality of shielding segments. In one example, the adjacent shielding segments are coupled with a ligament.

In one example, at least a portion of at least one shielding segment of the plurality of shielding segments overlies at least a portion of at least one adjacent shielding segment of the plurality of shielding segments when the prosthetic valve assembly is in a radially unexpanded configuration.

In one example, the at least one shielding segment does not overlap the at least one adjacent shielding segment when the prosthetic valve assembly is in a radially expanded configuration.

In one example, the shielding structure further includes a plurality of shielding ribs.

In one example, the plurality of shielding ribs are more rigid than the shielding segments.

In one example, the shielding ribs extend along a height of the shielding structure.

In one example, the shielding structure further includes a coiled member that is at least partially integrated with the plurality of shielding segments.

In one example, the shielding structure is supported with a reinforcing material.

In one example, the reinforcing material is arranged in a pattern to provide axial and circumferential support to the shielding structure.

In one example, the valve assembly includes a plurality of leaflets.

In one example, the plurality of leaflets are asymmetrically disposed about a central longitudinal axis of the prosthetic valve assembly.

In one example, each leaflet of the plurality of leaflets has a free edge that is flared.

In one example, each leaflet of the plurality of leaflets has an uncoupled mating edge positioned adjacent an uncoupled mating edge of an adjacent leaflet.

In one example, an expansion ratio of an outer diameter of the suture ring between a radially unexpanded and expanded configuration is about 1.5 to about 5.

In one example, the valve assembly is configured to accommodate annulus diameters ranging from about 5 millimeters to about 40 millimeters.

Still other aspects, embodiments, and advantages of these example aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Embodiments disclosed herein may be combined with other embodiments, and references to "an embodiment," "an example," "some embodiments," "some examples," "an alternate embodiment," "various embodiments," "one embodiment," "at least one embodiment," "this and other embodiments," "certain embodiments," or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION

Figure 1:
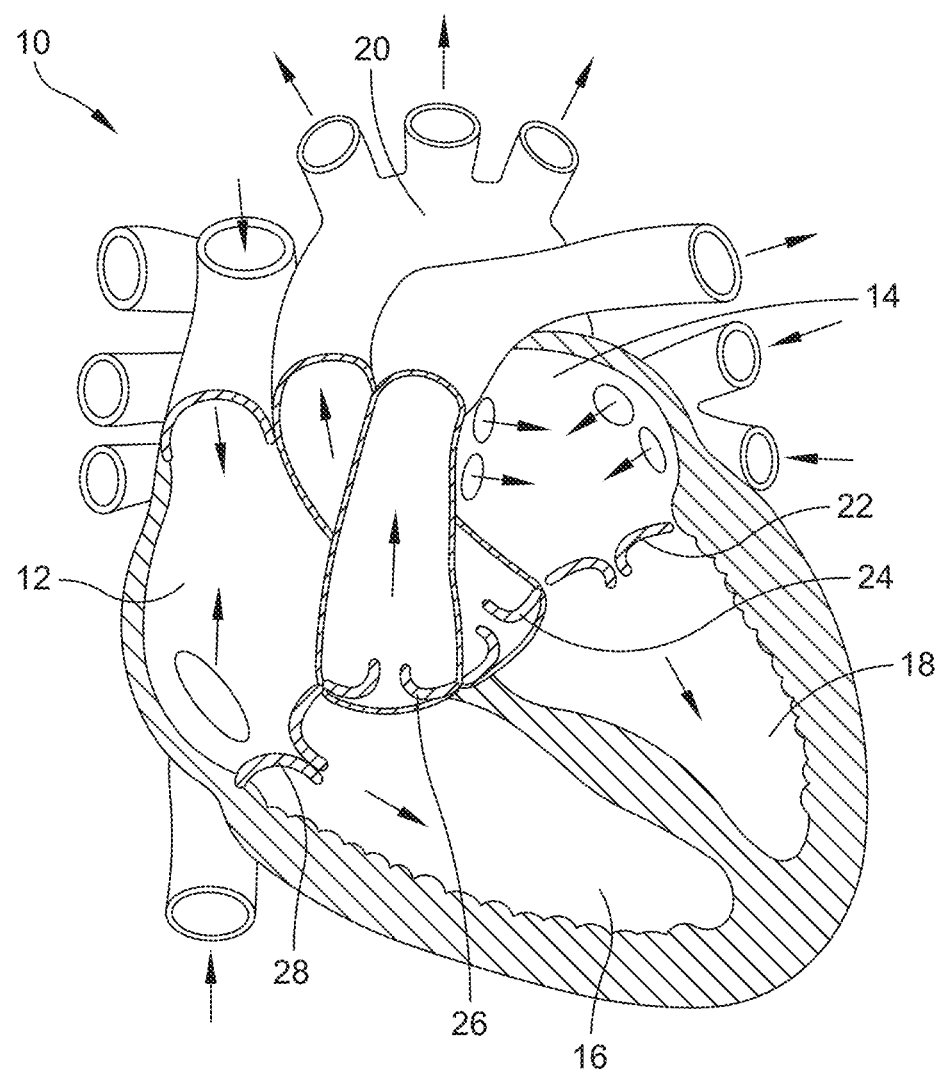
FIG. 1 is a schematic representation of a human heart showing the different locations where a prosthetic heart valve device may be positioned in accordance with one or more aspects of the invention.

Aspects of this disclosure relate to a growth-adaptive, or growth-accommodative, prosthetic valve assembly that provides replacement valve function in a patient without the need for post-implantation surgical intervention during a period of time when the patient's native valve annulus may be growing.

As described herein, a growth-adaptive prosthetic valve assembly has an outer diameter that is configured to adapt to a natural growing shape of a biological feature. In some embodiments, the growth adaptive prosthetic valve assembly of the present disclosure is capable of providing a radially expansive force that is sufficient to allow the outer diameter of the valve assembly to adapt to a natural growing shape of a biological feature. In some embodiments, the biological feature is the annulus of a heart valve.

Besides children, the disclosed valve assembly may be used in adult or non-growing patients, as well as non-human animals. The disclosed valve assembly is suitable for use in each of the four cardiac valve positions: mitral, aortic, tricuspid, and pulmonary. In some instances, the valve assembly may also be suitable for use in other locations of the body, such as the legs. According to various aspects, the disclosed valve assembly has diametrical expansion ratios ranging from about 1.5 to about 5, and can accommodate annulus diameters ranging from about 4 millimeters to about 40 millimeters.

In some embodiments, the valve assembly has diametrical expansion ratios ranging from about 1.6 to about 4.5. In some embodiments, the valve assembly has diametrical expansion ratios ranging from about 1.7 to about 4.0. In some embodiments, the valve assembly has diametrical expansion ratios ranging from about 1.7 to about 3.5. In some embodiments, the valve assembly has diametrical expansion ratios ranging from about 1.8 to about 3.0. In some embodiments, the valve assembly has diametrical expansion ratios ranging from about 1.9 to about 2.5. In some embodiments, the valve assembly has diametrical expansion ratios ranging from about 1.9 to about 2.2. In some embodiments, the valve assembly has diametrical expansion ratios ranging from about 1.9 to about 2.1. In some embodiments, the valve assembly has a diametrical expansion ratio of about 2.0. The diametrical expansion ratio may be selected based on the length of a time period during which the valve assembly is expected to be implanted in an annulus of a patient and the expected growth of the annulus during that time period.

In various embodiments, the valve assembly can be configured to accommodate annulus diameters based on the anatomical structure into which the valve assembly is to implanted, based on the expected growth of the anatomical structure of the patient over time. Studies of cardiovascular structure have shown that mean aortic diameter is 7 millimeters for a newborn, 14 millimeters for a six-year-old child, and is 22 millimeters for an adult; mean pulmonary valve diameter is 8 millimeters for a newborn, 16 millimeters for a six-year-old child, and is 26 millimeters for an adult; mean mitral valve diameter is 10 millimeters for a newborn, 19 millimeters for a six-year-old child, and is 28 millimeters for an adult; mean aortic root diameter is 10 millimeters for a newborn, 15 millimeters for a six-year-old child, and is 30 millimeters for an adult; and mean right pulmonary artery diameter is 6 millimeters for a newborn, 12 millimeters for a six-year-old child, and is 18 millimeters for an adult.

In some embodiments, the valve assembly can accommodate annulus diameters ranging from about 4 millimeters to about 40 millimeters. Of course, it is recognized that a valve assembly that can accommodate a larger annulus diameter may be required for a larger patient, while a valve assembly that can accommodate a smaller annulus diameter may be required for a smaller patient.

For example, in some embodiments for use in newborns, the valve assembly can accommodate annulus diameters ranging from about 4 millimeters to about 15 millimeters. In some embodiments, the valve assembly can accommodate annulus diameters ranging from about 7 millimeters to about 14 millimeters. In some embodiments, the valve assembly can accommodate annulus diameters ranging from about 7 millimeters to about 10 millimeters. In some embodiments for use in six-year-old children, the valve assembly can accommodate annulus diameters ranging from about 10 millimeters to about 20 millimeters. In some embodiments, the valve assembly can accommodate annulus diameters ranging from about 12 millimeters to about 18 millimeters. In some embodiments, the valve assembly can accommodate annulus diameters ranging from about 13 millimeters to about 17 millimeters. In some embodiments, the valve assembly can accommodate annulus diameters ranging from about 14 millimeters to about 16 millimeters. In some embodiments, the valve assembly can accommodate an annulus diameter of about 14 millimeters. In some embodiments, the valve assembly can accommodate an annulus diameter of about 15 millimeters.

In some embodiments for use in adults, the valve assembly can accommodate annulus diameters ranging from about 15 millimeters to about 30 millimeters. In some embodiments, the valve assembly can accommodate annulus diameters ranging from about 17 millimeters to about 28 millimeters. In some embodiments, the valve assembly can accommodate annulus diameters ranging from about 19 millimeters to about 26 millimeters. In some embodiments, the valve assembly can accommodate annulus diameters ranging from about 21 millimeters to about 25 millimeters. In some embodiments, the valve assembly can accommodate an annulus diameter of about 22 millimeters.

The leaflet-type of valve assembly associated with the embodiments described herein includes a segmented suture ring that is partially or fully circumferentially discontinuous between sites where it is attached to the native annulus of the patient. Segmentation of the suture ring between the attachment sites allows the valve assembly to grow to accommodate diametrical expansion of the annulus, which makes the device suitable for use in growing patients, such as pediatric patients. Components of the disclosed valve assembly that attach to the suture ring segments may also be fully segmented, partially segmented, or in the alternative may be circumferentially continuous, and are designed to enable operational functionality, i.e., competent opening and closing of the leaflets, over a range of annulus diameters.

The aspects disclosed herein in accordance with the present invention, are not limited in their application to the details of construction and the arrangement of components set forth in the following description or illustrated in the accompanying drawings. These aspects are capable of assuming other embodiments and of being practiced or of being carried out in various ways. Examples of specific implementations are provided herein for illustrative purposes only and are not intended to be limiting. In particular, acts, components, elements, and features discussed in connection with any one or more embodiments are not intended to be excluded from a similar role in any other embodiments.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated reference is supplementary to that of this document; for irreconcilable inconsistencies, the term usage in this document controls. Moreover, titles or subtitles may be used in the specification for the convenience of a reader, which shall have no influence on the scope of the present invention.

FIG. 1 is a schematic representation of a human heart 10. As shown in FIG. 1, the human heart includes two atria and two ventricles: a right atrium 12 and a left atrium 14, and a right ventricle 16 and a left ventricle 18. The heart 10 also includes an aorta 20. Disposed between the left atrium and the left ventricle is the mitral valve 22, which is a dual-flap (two leaflet) valve that opens as a result of increased pressure in the left atrium as it fills with blood. As atrial pressure increases, the mitral valve opens and blood passes into the left ventricle in the direction indicated by the arrow shown in FIG. 1. The aortic valve 24 has three leaflets and functions to maintain unidirectional blood flow between the left ventricle and the aorta. The aortic valve is effectively a one-way valve between the heart and the rest of the body since blood is pumped from the left ventricle, through the aortic valve, and down the aorta, which in turn supplies blood to all of the organs in the body. The pulmonary valve 26 is also a three leaflet valve and is positioned between the right ventricle and the pulmonary artery, which transports deoxygenated blood to the lungs from the heart. The tricuspid valve 28 is a three leaflet valve that forms the boundary between the right atrium and the right ventricle and functions to prevent back flow of blood into the right atrium.

Problems may occur with any one or more of the heart valves discussed above in human patients, including children. For instance, heart valve disease or congenital birth defects may cause the valve to function improperly or inadequately, such as by having holes or leaking, or the valve may be too narrow or completely closed. When this happens, a prosthetic valve assembly may be implanted into the patient to replace the defective valve. The prosthetic valve assemblies described below may be used to replace one or more of the native heart valves shown in FIG. 1.

Figure 2:
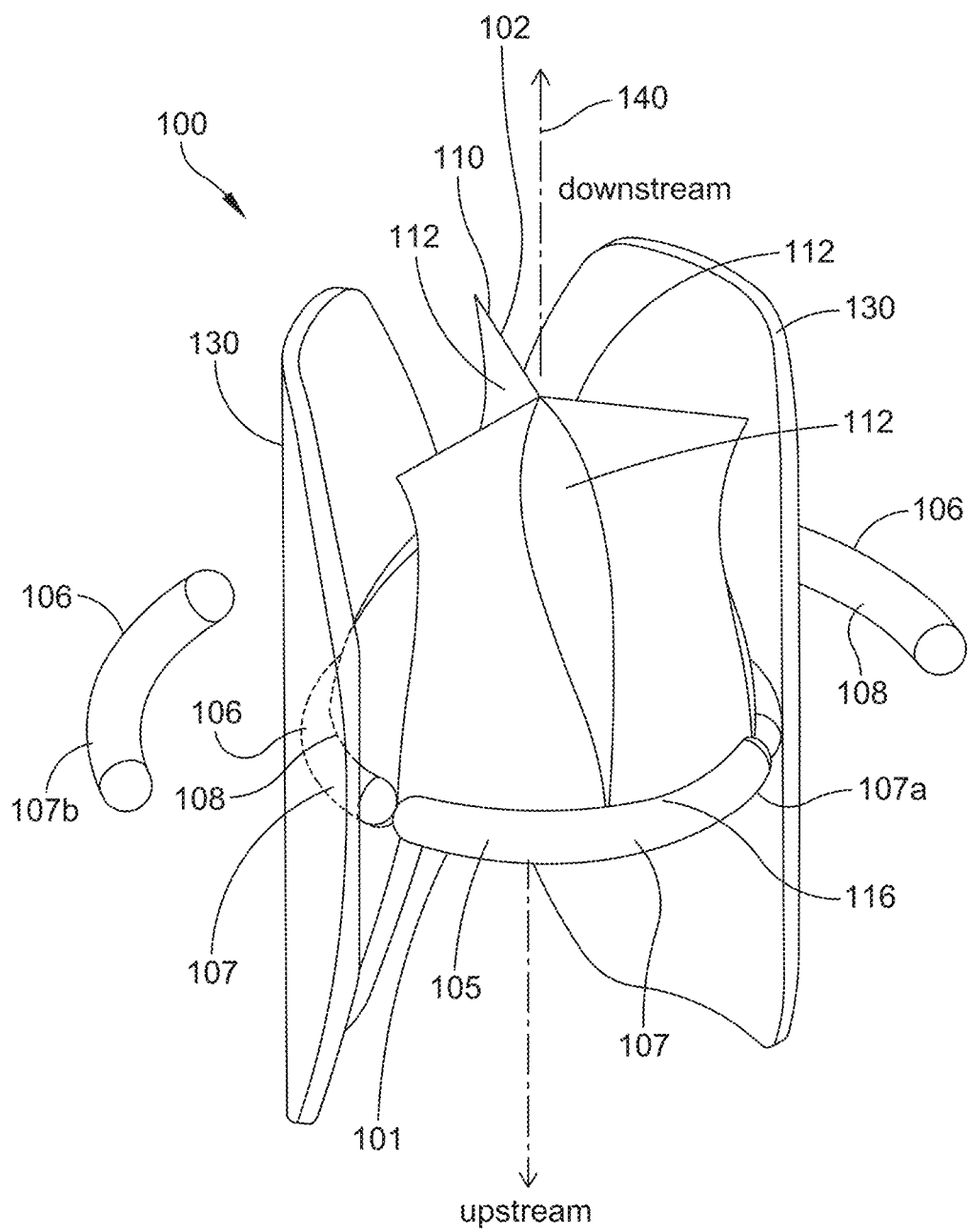
FIG. 2 is a perspective view of one example of a prosthetic valve assembly in accordance with one or more aspects of the invention.

FIG. 2 is a perspective view of one example of a prosthetic valve assembly, also referred to herein as simply "valve assembly," shown generally at 100, in accordance with at least one embodiment of the present disclosure. The prosthetic valve assembly 100 may be used for controlling fluid flow in an annulus, including any one of the valve locations in the heart discussed above in reference to FIG. 1. As indicated in FIG. 2, fluid flows through the valve assembly 100 from the upstream side 101 to the downstream side 102. The prosthetic valve assembly 100 includes a suture ring 105 formed from two or more segments 107 and a leaflet subassembly 110 that includes at least one leaflet 112 configured for controlling a flow of fluid through the valve assembly 100. The perspective view of FIG. 2 shows the downstream side of the leaflet subassembly.

The suture ring 105 includes two or more segments 107, and the example shown in FIG. 2 has three segments, but it is to be appreciated that suture rings with greater than three segments is within the scope of this disclosure. For instance, the suture ring 105 may have four to ten segments.

According to one embodiment, the segments 107 have a circular cross-section. In some embodiments, the cross-sectional area of the segments, and the ratio of the cross-sectional area to the minimum and maximum diameter of the suture ring is selected so that the cross-sectional area of the segment does not interfere with blood flow through the valve assembly, while also allowing the segment to provide sufficient structural support to the valve assembly. The cross-sectional area of the segment may be in a range of 0.002 square millimeters to 3.2 square millimeters. In some embodiments, the cross-sectional area of the segment may be in a range of 0.01 square millimeters to 3.0 square millimeters. The cross-sectional area of the segment may be in a range of 0.1 square millimeters to 2.5 square millimeters. The cross-sectional area of the segment may be in a range of 0.5 square millimeters to 2.0 square millimeters. The cross-sectional area of the segment may be in a range of 1.0 square millimeters to 1.5 square millimeters. The cross-sectional area of the segment may be in a range of 1.0 square millimeters to 1.2 square millimeters. In some embodiments, the cross-sectional area of the segment may correspond to about 1.0% to about 5.0% of the minimum and maximum diameter of the suture ring 105. In some embodiments, the cross-sectional area of the segment may correspond to about 1.5% to about 4.5% of the minimum and maximum diameter of the suture ring 105. In some embodiments, the cross-sectional area of the segment may correspond to about 2.0% to about 4.0% of the minimum and maximum diameter of the suture ring 105. In some embodiments, the cross-sectional area of the segment may correspond to about 2.5% to about 3.5% of the minimum and maximum diameter of the suture ring 105. In some embodiments, the cross-sectional area of the segment may correspond to about 3.0% of the minimum and maximum diameter of the suture ring 105.

According to some embodiments, the suture ring segments 107 may have ridges or grooves or other features, such as dovetail joints, included in one or more portions of their surface that aid in attaching and/or mating one or more elements of the leaflet subassembly 110 to the segment 107.

Once implanted into the patient, the segments 107 of the suture ring 105 may be sutured, stapled or otherwise attached to the native annulus tissue. According to one embodiment, each of the segments 107 has an outer portion 106 that is configured to attach to the annulus 150. This is demonstrated in the example shown in FIG. 5A, where a valve assembly 200 (discussed further below) is positioned in an atrioventricular position of a heart. The outer portion 206 of the suture ring 205 is configured for attachment to the annulus 150.

The suture ring 105 may be constructed from any one of a number of suitable biocompatible materials, such as polymers, including biopolymers and synthetic polymers, metals and metal alloys, fixed xenograft or homograft tissue such as porcine or bovine pericardium, or a hybrid material that includes a combination of two or more of these materials, such as a metal alloy encapsulated with a tissue material or polymer. Non-limiting examples of polymer include polyester material such as DACRON®. Non-limiting examples of metal alloys include platinum-iridium alloy, cobalt chromium alloy, and shape memory alloys such as nitinol (made from nickel and titanium).

Figure 3:
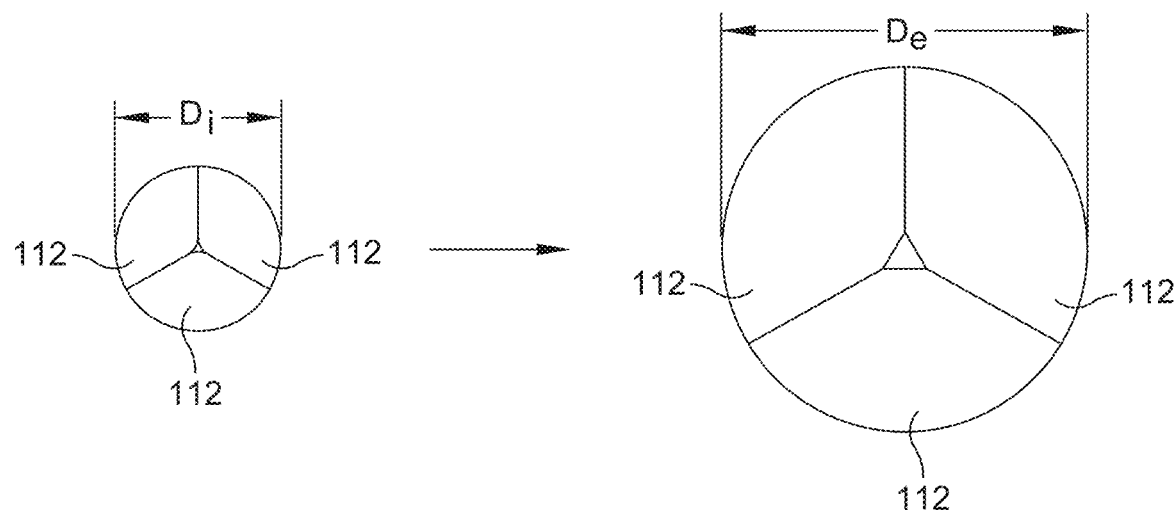
FIG. 3 is a plan view of a representation of an expansion capability of a prosthetic valve assembly according to one or more aspects of the invention.

Segmenting the suture ring 105 into individual segments 107 allows the suture ring 105 to expand as the diameter of the annulus grows larger over time, i.e., as the patient grows. According to some embodiments, the suture ring 105 allows a diameter of the valve assembly 100 to expand or otherwise increase from an initial implanted diameter to a final expanded diameter. In accordance with one embodiment, the ratio of the diameter of the valve assembly at the initial implanted position or radially unexpanded configuration to the diameter of the valve assembly at the final expanded position or radially expanded configuration is greater than one. This ratio, also referred to herein as the "diametrical expansion ratio" or simply "expansion ratio" in some embodiments is about 1.5 to about 5, as discussed above. A representation of the expansion ratio is shown in FIG. 3, which shows an initial implanted diameter, $D_i$, and a final expanded diameter, $D_e$. In certain embodiments, the suture ring 105 has an outer diameter that defines the diameter of the valve assembly. For instance, the valve assembly 100 shown in FIG. 2 shows the three segments 107 of the suture ring 105 in both a compact state 107a (shown attached to the leaflet subassembly 110), and in an expanded state 107b (front segment not shown). For purposes of simplification, the expanded state of the suture ring 105 shown in FIG. 2 does not include the leaflet subassembly 110 attached to the suture ring 105. In other embodiments, a shielding structure 130 (discussed further below) may define the diameter of the valve assembly.

According to one embodiment, the segments 107 may be fabricated or otherwise configured such that the radius of curvature expands from an initial implanted configuration to match or exceed the fully expanded diameter of the valve assembly. In some embodiments, the segments 107 may also be configured to provide a small restoring spring force when they are elastically deformed to conform to a diameter that is smaller than the fully expanded diameter value, which may help ensure continued expansion of the device as the patient's annulus grows. Thus, the suture ring segments 107 may be configured to exert a smaller outward pressure or force to aid in expansion.

In accordance with at least one embodiment, the valve assembly 100 may be configured to accommodate annulus diameters in a range of from about 4 millimeters to about 40 millimeters, as discussed above. An initial implanted diameter and final expanded diameter of the valve assembly may therefore also be within a range of from about 4 millimeters to about 40 millimeters, depending on the desired expansion ratio.

Referring again to FIG. 2, the valve assembly 100 also includes a leaflet subassembly 110. According to at least one embodiment, the leaflet subassembly 110 is attached to an inner portion 108 of at least one segment 107 of the suture ring 105. The leaflet subassembly 110 may be attached to one or more of the segments 107 of the suture ring 105 using any one of a number of different attachment methods, including sutures or staples. In some embodiments, the leaflet subassembly 110 and the suture ring 105 may form a continuous structure. For instance, the leaflet subassembly 110 and the suture ring 105 may be formed from a single piece of material or materials.

Figure 4:
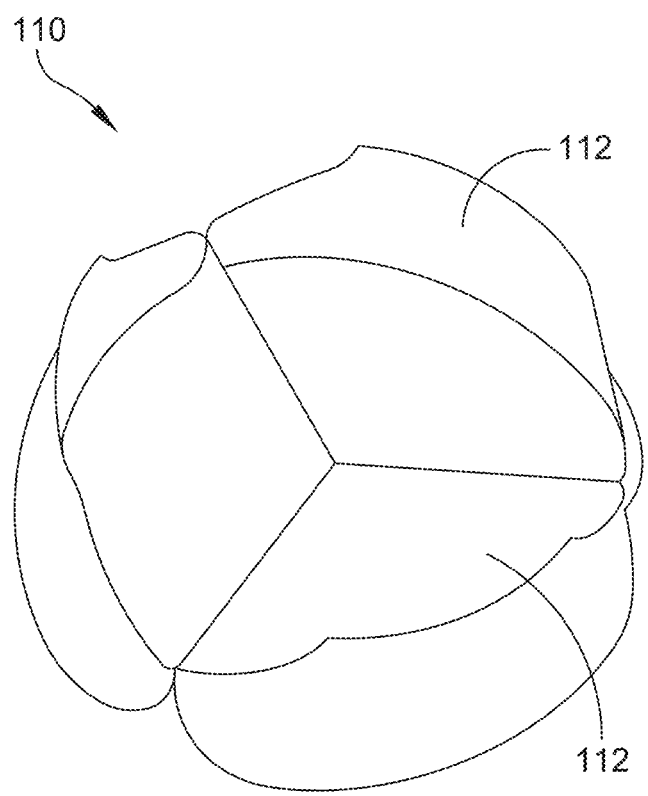
FIG. 4 is a perspective view of another example of a prosthetic valve assembly in accordance with one or more aspects of the invention.

The leaflet subassembly 110 includes at least one leaflet 112 that is configured for controlling a flow of fluid through the prosthetic valve assembly 100. The leaflet subassembly 110 shown in FIG. 2 includes three leaflets 112. Referring to FIG. 4, a perspective view of the upstream side of a leaflet subassembly 110 is shown. The leaflet subassembly 110 in this example includes three leaflets 112. Other numbers of leaflets are also within the scope of this disclosure. For instance, the leaflet subassembly may include between one and ten leaflets. In some embodiments, the leaflet subassembly 110 has two or three leaflets 112. The leaflets 112 may be symmetrically or asymmetrically disposed about a central longitudinal axis 140 of the valve assembly 100. The example shown in FIG. 2 has leaflets 112 arranged in a symmetrical arrangement. The leaflets 112 of the leaflet subassembly 110 may be fabricated from a single, continuous piece of material, joined to one another, or may be wholly separate pieces.

According to at least one embodiment, the number of segments 107 included in the suture ring 105 may be the same number of leaflets 112 included in the leaflet subassembly 110. In some embodiments, each of the leaflets 112 may be attached to one or more segments 107 of the suture ring 105. According to at least one embodiment, at least one leaflet 112 includes an outer edge 116 configured to attach to the inner portion 108 of the segment 107. In some embodiments, the leaflets 112 and the suture ring 105 form a continuous structure. For instance, in some embodiments, the leaflets 112 and the suture ring 105 are continuously fabricated as a single piece.

The leaflet subassembly 110 may be constructed from any one of a number of biocompatible materials, including fixed xenograft or homograft tissue, such as bovine, porcine, or human pericardium, non-composite or composite synthetic polymers such as GORE-TEX® material, silicone, polytetrafluoroethylene (PTFE), poly(styrene-b-isobutylene-b-styrene (SIBS), polyester such as DACRON® material, living tissue induced to grow on a non-living scaffold or substrate material, or a combination thereof.

In some embodiments, the leaflets are made of material that is selected for its biocompatibility and/or flexibility.

In some embodiments, the leaflets have a thickness in the range of about 15 to about 500 microns. In some embodiments, the leaflets have a thickness in the range of about 50 to about 450 microns. In some embodiments, the leaflets have a thickness in the range of about 100 to about 400 microns. In some embodiments, the leaflets have a thickness in the range of about 150 to about 350 microns. In some embodiments, the leaflets have a thickness in the range of about 200 microns to about 300 microns. In some embodiments, the leaflets have a thickness in the range of about 200 microns. In some embodiments, the leaflets have a thickness in the range of about 250 microns. In some embodiments, the leaflets have a thickness in the range of about 300 microns. If the leaflets are too thin, they will not have sufficient durability. If the leaflets are too thick, they will not close properly.

According to one embodiment, the leaflets 112 may include reinforcement elements such as ribs fabricated from identical or dissimilar material(s) as the leaflet, such as polymers or metal alloys. The reinforcement elements may be function to add preferential structural stiffness tuning or as spring tensioning elements to aid in valve expansion. In one embodiment, the reinforcement features include macrostructural features, which include relatively large dimensions, e.g., dimensions measured in millimeters or microns, and may in some instances form a regular or irregular pattern. The reinforcement elements of the leaflets 112 may include chopped fiber, plain woven, non-woven, and/or unidirectional fiber, or any other weave pattern, such as satin (e.g., 8 harness satin) or twill.

Figure 5A:
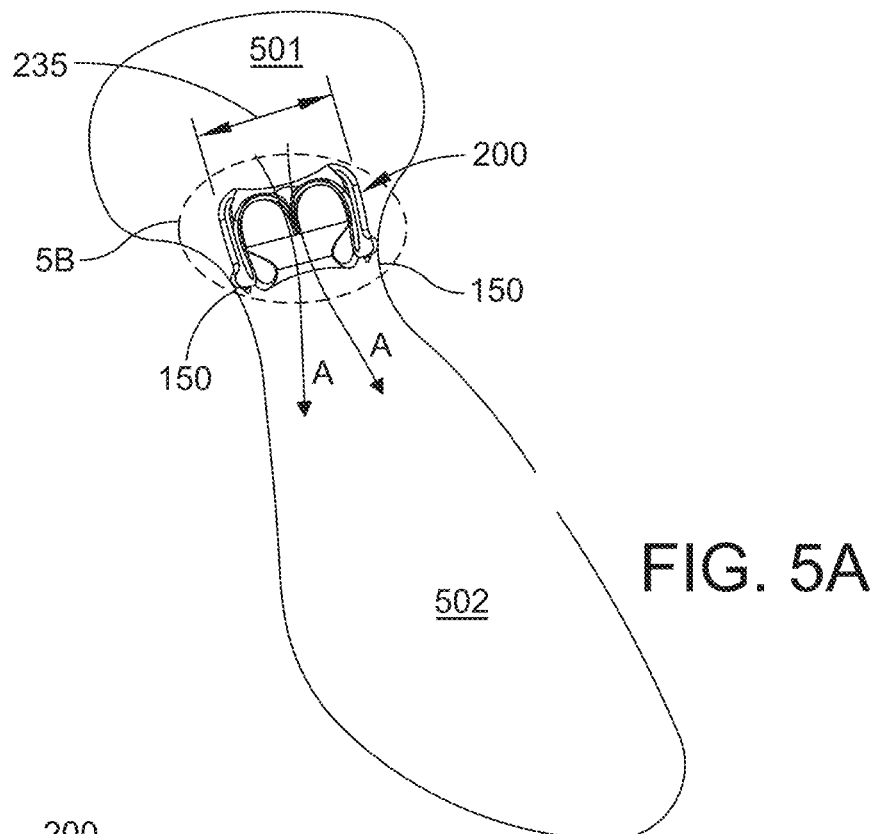
FIG. 5A is a cross-sectional side view of another example of a prosthetic valve assembly positioned in an atrioventricular location of a heart in accordance with one or more aspects of the invention.
Figure 5B:
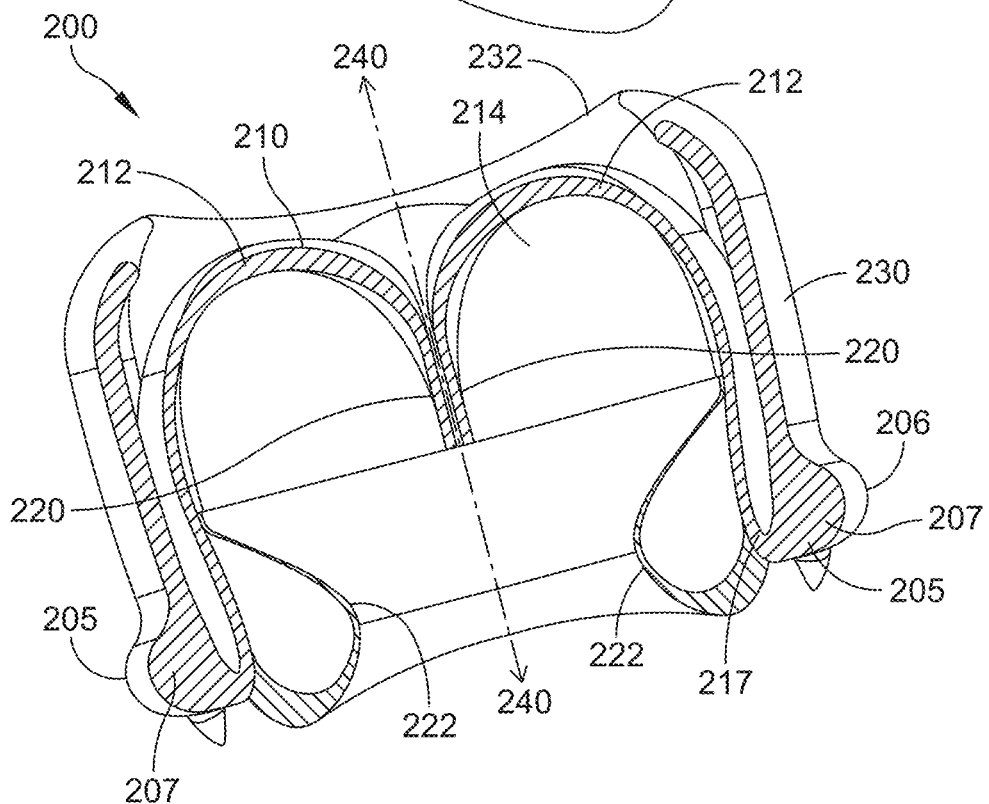
FIG. 5B is an enlarged view of the prosthetic valve assembly of FIG. 5A.

FIGS. 5A and 5B show a cross-sectional side view of another example of a valve assembly 200 in accordance with another embodiment of the present disclosure. The valve assembly 200 shown in FIGS. 5A and 5B is shown in the expanded configuration. The valve assembly 200 shown in the enlarged view of FIG. 5B shares some commonalities with the valve assembly 100 of FIG. 2. For example, the valve assembly 200 has a segmented suture ring 205 and a leaflet subassembly 210 that includes at least one leaflet 212. In the example shown in FIG. 5B, the suture ring 205 includes three segments 207 (the third segment positioned in the back is not shown) and the leaflet subassembly 210 includes three leaflets 212. The leaflets 212 are positioned or otherwise disposed symmetrically about the central longitudinal axis 240 of the valve assembly 200. At least a portion of each leaflet 212 is attached to a corresponding segment 207 of the suture ring 205, as shown in FIG. 5B. FIG. 5B shows an attachment feature 217 between the leaflet 212 and the corresponding segment 207. In certain embodiments, the leaflet 212 and the segments 207 of the suture ring 205 form a continuous structure, i.e., form a single piece.

The valve assembly 200 also includes a sinus structure 214, also referred to herein as an "artificial sinus," or simply "sinus." The sinus structure 214 is a "pocket" like formation on the downstream side surface of the leaflets 212 and functions to ensure sealing around the outer edges of the leaflets as the valve assembly expands.

The valve assembly 200 also includes a shielding structure 230. The shielding structure 230 may be attached to the suture ring 205 and functions to protect the leaflets 212 from exposure to environmental conditions that may detrimentally affect the leaflets 212. For instance, the shielding structure 230 may be configured to protect the leaflets 212 from environmental conditions that threaten to detrimentally impact the functionality of the leaflets 212 or other components of the leaflet subassembly. For instance, the shielding structure 230 may protect the leaflets 212 from calcification or scar tissue overgrowth that would otherwise degrade the performance, structural integrity, or durability of the valve assembly 200. The shielding structure 230 is configured to extend laterally between the leaflets 212 and the annulus 150 (see FIG. 5A).

In some embodiments, the shielding structure 230 may be defined by a plurality of shielding segments 232. In some embodiments, at least a portion of each shielding segment 232 is attached to a segment 207 of the suture ring 205. The shielding segments 232, in a similar manner as the suture ring segments 207, may be configured to contribute a small restoring force by being constructed such that their expanded radius of curvature matches or exceeds that of the fully expanded radius of curvature of the valve assembly. Thus, the shielding segments 232 may be configured to exert a smaller outward pressure or force to aid in expansion.

The shielding structure 230 may be constructed from any one or more of a number of biocompatible materials, including those discussed above in reference to the suture ring and leaflet subassembly. For example, the shielding structure 230 may be formed from a biocompatible metal or metal alloy, such as a platinum-iridium alloy or a cobalt-chromium alloy, and/or from a polymer material, such as GORE-TEX®, DACRON®, or TEFLON®. According to some embodiments, one or more components of the shielding structure 230 may be constructed from a different biocompatible material than the leaflet 212. According to at least one embodiment, the shielding structure 230 may have a laminated structure. For instance, the shielding structure 230 may be formed of two or more layers of similar or dissimilar materials.

The example shown in FIGS. 5A and 5B includes a shielding structure 230 that includes three shielding segments 230, which in this instance is also the same number of suture ring segments 207, but it is to be appreciated that the numbers of each of these features need not be identical. For instance, the number of suture ring segments 207, leaflets 212, and shielding segments 232 may be equal in number, derived as integer multiple counts (e.g., 3 leaflets, 9 suture ring segments, and 6 shielding segments), or other configurations.

In accordance with at least one embodiment, one or more components of the shielding structure 230, including the shielding segments 232, may be constructed to be more rigid than the leaflet 212. Rigidity can be implemented via a material and/or structure, for instance, by using a more rigid material, implementing ribs or other structural features, or by varying the local geometry (e.g., using a denser construction) by thickening a local cross-section of the material. In some instances the shielding structure 230 may have a Young's modulus that is larger than a Young's modulus of the leaflet 212. In other embodiments, the shielding structure 230 may include internal reinforcement elements that add rigidity.

According to some embodiments, the suture ring 205, the leaflets 212, and the shielding structure 230 may form a continuous structure. For instance, the example shown in FIG. 5B illustrates a single piece construction for the leaflets 212, shielding structure 230 and segmented suture ring 205, although these components may be constructed from different materials. According to some embodiments, the leaflet subassembly 210 and the shielding structure 230 may form individual pieces that are independently attached to the segments 207 of the suture ring 205.

The shielding segments 232 may be continuous with the other components of the valve assembly 200, such as the leaflet subassembly 210 or the suture ring segments 207, or may be formed separately and then attached to outer surfaces of the suture ring segments 207, leaflet subassembly 210, and/or annulus tissue. In addition, the shielding segments 232 may circumferentially overlap when the valve assembly is in the unexpanded configuration such that continuous shielding may be provided as the tissue annulus grows and the annulus of the diameter increases.

FIG. 5A is a cross-sectional view of the valve assembly 200 placed in an atrioventricular location of a heart. The valve assembly 200 is oriented so that the upstream end of the valve faces the atrium 501 and the downstream end of the valve faces the ventricle 502. As previously discussed, an outer portion of the segments of the suture ring is attached to the annulus 150, and is therefore configured to expand from an initial implanted diameter to a final expanded diameter as the annulus 150 increases in diameter, i.e., as the patient grows. According to some embodiments, other portions of the valve assembly 200 are configured to adapt, e.g., their structures have a dynamic geometry that adapts to the radial outward expansion of the segmented suture ring 205. For instance, the leaflets 212 may include folds of extra material that allow the leaflets 212 to maintain their functionality as the suture ring 205 expands. As shown in FIG. 5B, according to some embodiments, the leaflet 212 may have a free edge 222 that is flared or slightly splayed. This feature functions to preserve leaflet functionality when the downstream edges of the shield segments 232 are folded during the time period the suture ring 205 is not at the fully expanded configuration (discussed further below in reference to FIG. 7C).

In some embodiments, portions of the valve assembly 200 may remain in a more fixed state, e.g., their structures have a static geometry that is maintained as the segmented suture ring 205 radially expands. For example, an upstream diameter 235 of the shielding structure 230 may have substantially the same value as the suture ring 205 expands outwardly. This may be due in part to the location of the upper portion of the shielding structure 230. For instance, the upper portion of the shielding structure 230 may at least partially extend into a chamber of the heart, where it is minimally subjected to compressive and/or expansive forces. Other positions of the valve assembly 200 within the annulus are also within the scope of this disclosure. For instance, the device may be positioned such that the upstream diameter 235 of the shielding structure 230 is positioned within the annulus, and does not extend into a chamber of the heart, or may extend to a lesser amount than that shown in FIG. 5A.

Figure 6:
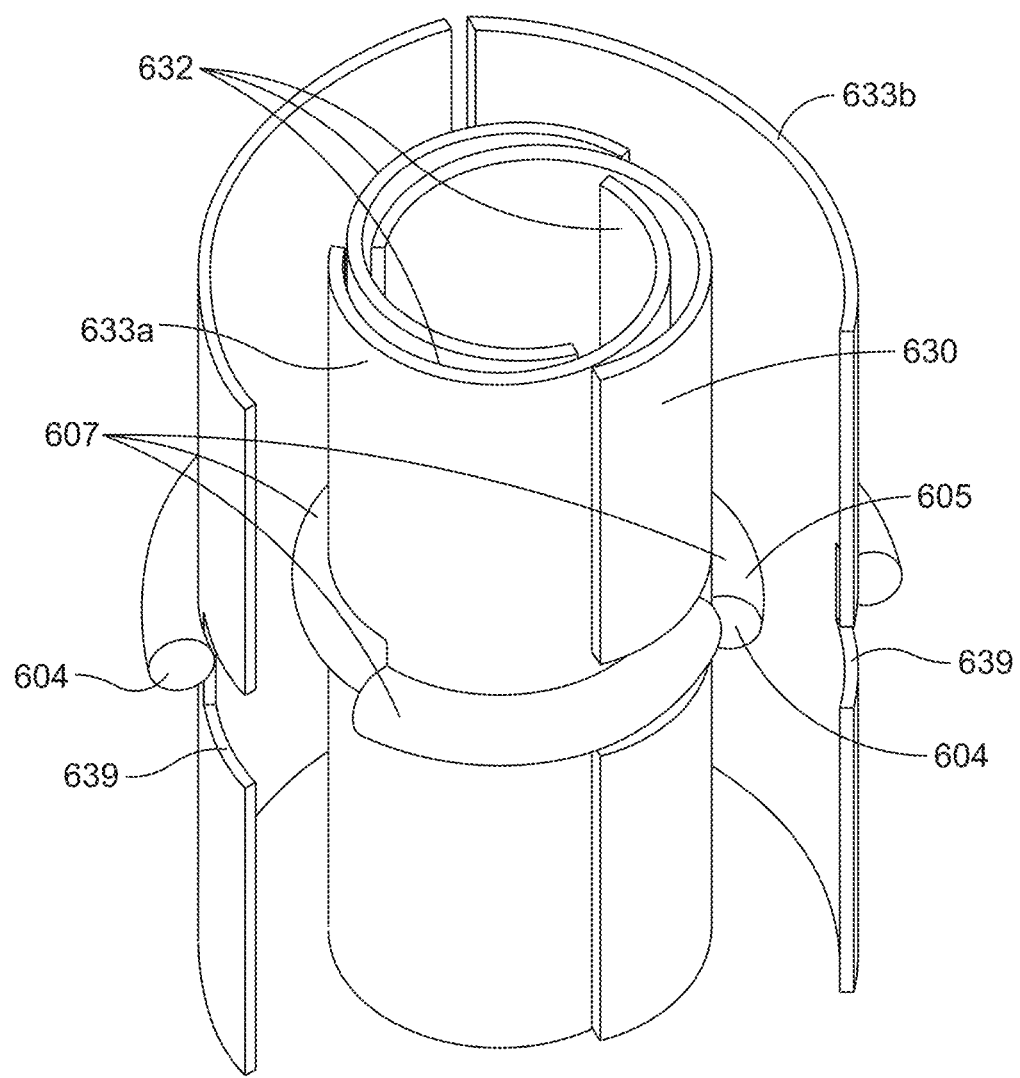
FIG. 6 is a perspective view of one example of a shielding structure and a suture ring in unexpanded and expanded configurations in accordance with one or more aspects of the invention.

Referring now to FIG. 6, a shielding structure 630 and a suture ring 605 according to some embodiments are shown in both an unexpanded configuration 633a and an expanded configuration 633b. According to this embodiment, the shielding structure 630 includes three shielding segments 632 and the suture ring 605 includes three segments 607 such that each shielding segment 632 is attached to a corresponding segment 607 of the suture ring 605. In some instances, the segment 607 may be attached such that it is physically centered on the shielding segment 632. For instance, the suture ring segment 607 may be centered along the length and/or height of the shielding segment 632. In the radially unexpanded configuration, i.e., when the device is first implanted, the segments 607 of the suture ring 605 may be configured to be close to one another. For example, an end portion 604 of each segment 607 may be positioned immediately adjacent to an end portion of an adjacent segment, and in some instances, adjacent end portions may be in physical contact with one another such that the suture ring 605 forms one continuous ring. In other instances, there may be a small gap between the end portions 604 of the segments 607 when the suture ring 605 is in the unexpanded state.

The shielding segments 632 of the shielding structure 630 of FIG. 6 are physically separated from one another, but in the radially unexpanded configuration at least a portion of at least one shielding segment 632 overlies at least a portion of at least one adjacent shielding segment 632. For instance, the shielding segments 632 may form a "nested" configuration in the unexpanded state. According to some embodiments, one or more of the shielding segments 632 may include an alignment feature 639, such as a notch or groove or slit, that allows the shielding segments 632 to overlap in the unexpanded configuration and accommodate the corresponding, attached segments 607, as shown in FIG. 6. The overlapping of the shielding segments 632 may also allow the device to compact to a smaller viable diameter, which increases the circumferential coverage capability or the range of annulus diameters that can be provided by the device in the expanded state.

As the segments 607 of the suture ring 605 radially expand to accommodate the growth of the annulus 150, the overlapping portions of the shielding segments 632 becomes smaller as they also move outward with their respective attached segment 607. In the fully expanded configuration, the shielding segments 632 do not overlap an adjacent shielding segment. In addition, the segments 607 of the suture ring 605 are spaced apart from one another such that the respective end portions 604 are not in physical contact with one another.

Figure 7A:
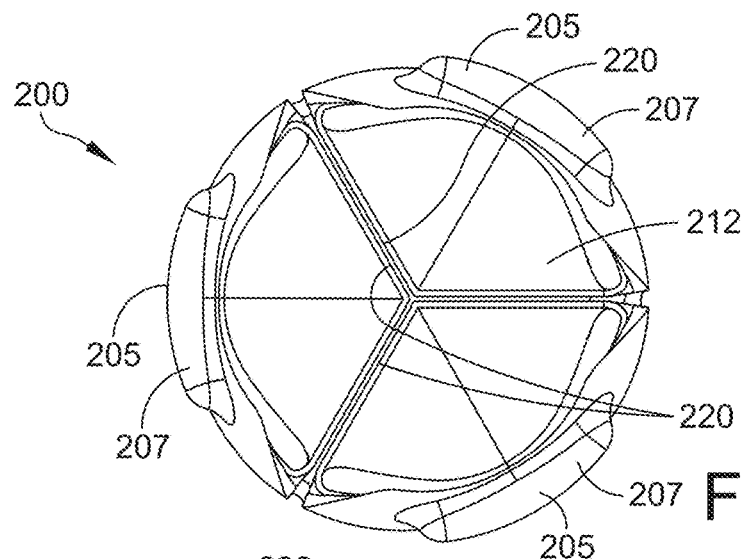
FIG. 7A is a plan view of a downstream side of the prosthetic valve assembly shown in FIGS. 5A and 5B.
Figure 7B:
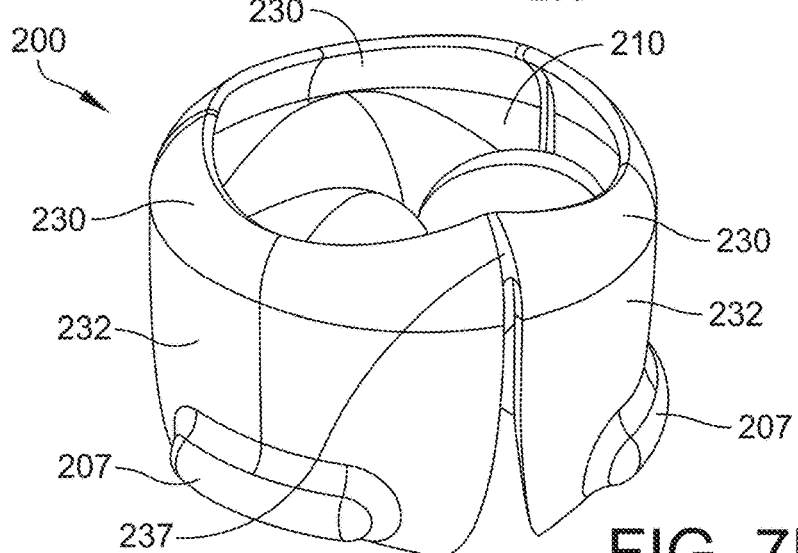
FIG. 7B is a perspective view of an upstream side of the prosthetic valve assembly of FIGS. 5A and 5B.
Figure 7C:
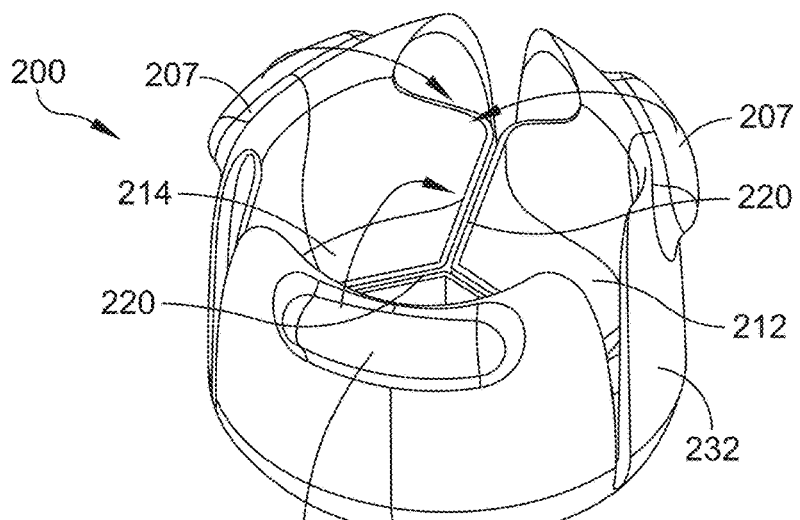
FIG. 7C is a perspective view of a downstream side of the prosthetic valve assembly of FIGS. 5A and 5B.

Referring now to FIGS. 7A-7C, other views of the valve assembly 200 shown in FIGS. 5A and 5B are shown. FIG. 7A is a plan view of a downstream side of the valve assembly 200, FIG. 7B is a perspective view of an upstream side of the valve assembly 200, and FIG. 7C is a perspective view of a downstream side of the valve assembly 200. All three views show the valve assembly 200 in the expanded configuration. According to at least one embodiment, a portion of a shielding segment 232 may be coupled to an adjacent shielding segment. The shielding segments 232 may therefore be partially segmented. For instance, as shown in FIG. 7B, adjacent shielding segments 232 may be coupled with a ligament 237 or other joining feature. The ligament 237 may be positioned at the upper, upstream end of the shielding structure 230 such that the shielding segments 232 and ligaments 237 form a continuous ring at the upstream end of the valve assembly 200. This configuration may provide added structural integrity to the shielding structure 230 and may add additional protection to the leaflets 212 from detrimental environmental influences.

Referring to FIGS. 5B, 7A, and 7C, each leaflet 212 has an uncoupled mating edge 220 positioned adjacent an uncoupled mating edge of an adjacent leaflet. This uncoupled structure allows for the leaflets to have an open position for permitting fluid flow in a downstream direction along arrows A as shown in FIG. 5A and a closed position for blocking fluid flow in an upstream direction.

Referring now to FIG. 7C, when in the initial implanted unexpanded configuration, the downstream end of the valve assembly 200 that includes the segments 207 of the suture ring 205 are positioned close to one another, as indicated by the arrows in FIG. 7C. The downstream end of the valve assembly 200 includes suture ring 205 and has a smaller diameter than the upstream end.

Figure 8A:
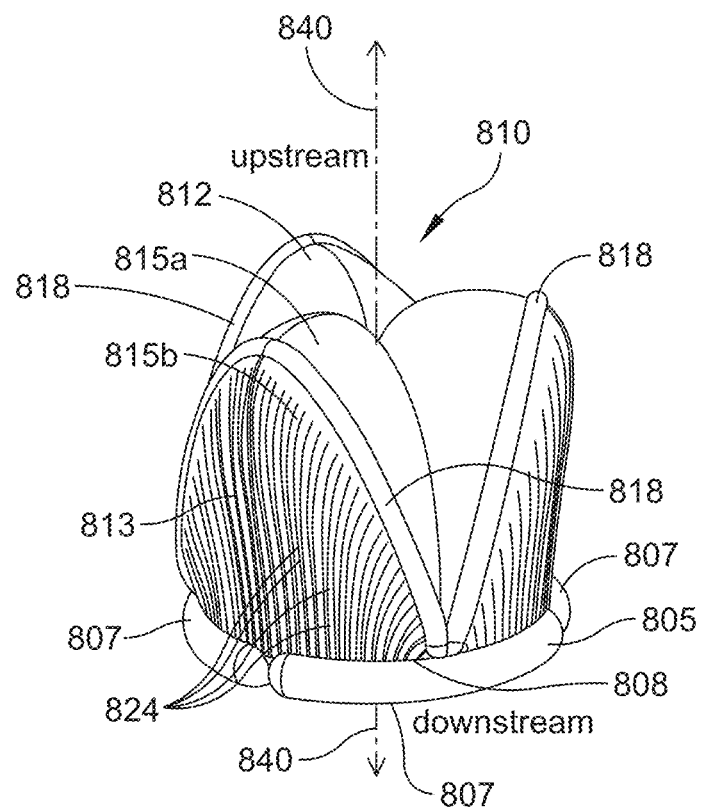
FIG. 8A is a perspective view of one example of a leaflet subassembly and suture ring in an unexpanded configuration in accordance with one or more aspects of the invention.
Figure 8B:
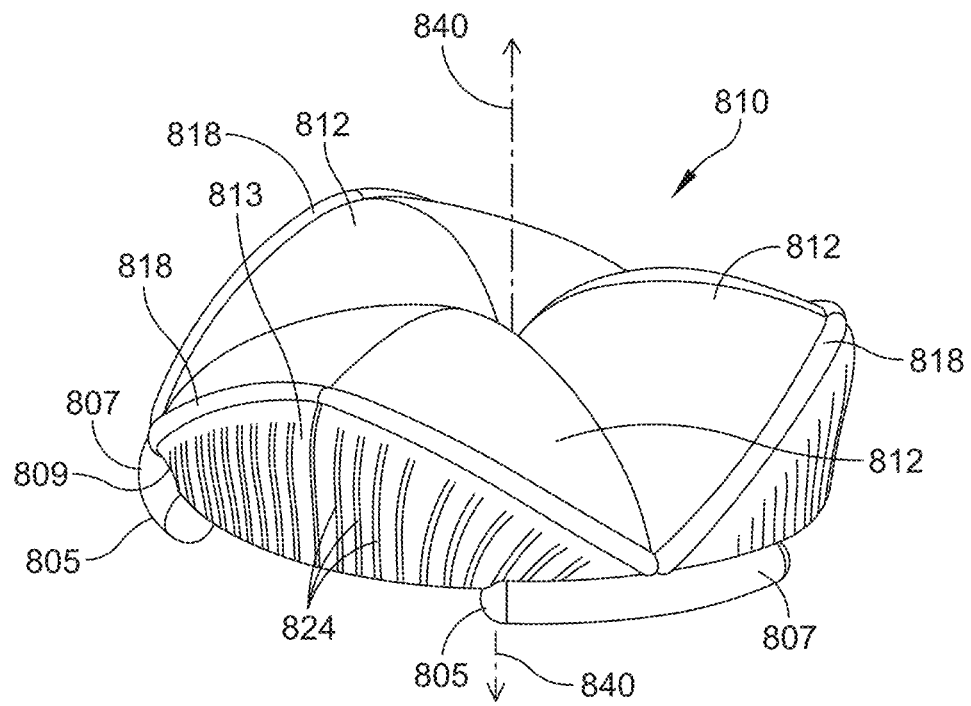
FIG. 8B is a perspective view of the leaflet subassembly and suture ring of FIG. 8A in an expanded configuration.

According to one embodiment, the leaflet subassembly includes a spring rib. One example of such a configuration is shown in FIGS. 8A and 8B. FIG. 8A is an unexpanded configuration of a leaflet subassembly 810 having three leaflets 812. The leaflet subassembly 810 also includes three spring ribs 818 that are coupled to the leaflet 812. As shown, the spring rib 818 forms a border between a first portion 815a and a second portion 815b of the leaflet 812 such that each portion 815a and 815b of the leaflet 812 is attached to the spring rib 818.

The spring rib 818 is also attached to the inner portion 808 of at least one segment 807 of the suture ring 805. The suture ring 805 has three segments 807 and each leaflet 812 has a corresponding spring rib 818. One end of the spring rib 818 is attached to one segment 807 of the suture ring 805, and the other end of the spring rib 818 is attached to an adjacent segment of the suture ring. The three spring ribs 818 of the example shown in FIG. 8A are configured to attach to the inner portion 808 of the segment 807 such that they are attached at a center of the length of the segment 807. According to alternative embodiments, the spring rib 818 is not attached to the segment 807 of the suture ring 805. For instance, the spring rib 818 may terminate at a position above the segment 807, and the surface 813 of the leaflet 812 may attach to the inner portion 808 of the suture ring segment 807. As shown in the unexpanded configuration of FIG. 8A, each segment 807 of the suture ring 805 terminates at an approximate mid-portion or center of the second portion 815b of the leaflet 812. In some embodiments, a section of the second portion 815b of the leaflet 812 may attach to the inner portion 808 of the suture ring segment 807. In other embodiments the suture ring segment 807 is not attached to the leaflet 812, and the spring rib 818 is attached to the suture ring segment 807.

In the unexpanded state, as shown in FIG. 8A, the spring ribs 818 are compressed and are thus configured to store energy that is released over time as an outward or radially expansive force. This force exerts pressure on the annulus that aids in accommodating the growth of the patient. The spring ribs 818 also aid in adding structural integrity to the valve assembly. In the compressed state, the spring ribs 818 extend in the upstream direction such that they extend along a longer length of the central longitudinal axis 840 of the valve assembly than in the expanded uncompressed state, as shown in FIG. 8B.

The spring ribs 818 may be constructed from one or more biocompatible materials, including biocompatible metals, metal alloys such as platinum-iridium alloy, cobalt chromium alloy, and shape memory alloys such as nitinol, and polymers. In some embodiments, the spring ribs 818 may be encapsulated with a material such as a polymer. For instance, the spring rib 818 may be constructed as a wire material that is encapsulated in a polymer. The spring ribs 818 may be formed as a round, conical, and/or flat wire having geometries (e.g., diameter, length) that correspond to the desired "spring-like" energy stored in the spring rib 818.

According to at least one embodiment, a surface 813 of the leaflet 812 may include expansion elements. One example of this feature is shown in FIGS. 8A and 8B, where the surface 813 of the leaflet 812 has a plurality of expansion elements 824. The expansion elements 824 may function to allow the leaflet 812 to be compressed circumferentially to reduce its effective circumference and accommodate the unexpanded configuration of the suture ring 805. In some instances, the expansion elements 824 may also reduce the effective thickness of at least a portion of the leaflet 812 (e.g., the second portion 815b that is adjacent the annulus or shielding structure). According to some embodiments, the expansion elements 824 may include pleats or folds that can be ether uniformly or non-uniformly expanded as the suture ring 805 expands radially outward. In at least one embodiment, the entire surface 813 of the leaflet 812 includes expansion elements 824, as shown in FIGS. 8A and 8B. In other embodiments, a portion of the surface of the leaflet includes expansion elements. In the example shown in FIGS. 8A and 8B, the plurality of expansion elements 824 form an accordion shape, where a series of alternating fold lines extend across the surface 813 of the leaflet 812.

FIG. 8B shows a fully expanded configuration of the leaflet subassembly 810 and suture ring 805 of FIG. 8A. As described above, the suture ring segments 807 are attached to the annulus, which expands over time as the patient grows. As shown, the spring ribs 818 radially expand outward with the suture ring segments 807 such that their length along the central longitudinal axis 840 is reduced. In addition, the surface 813 of the leaflet 812 also radially expands outward via the expansion elements 824 which expand into a relatively flattened position.

According to some embodiments, portions of the surface of the suture ring segments include mating features that aid in coupling one or more components of the leaflet subassembly to the segment. Non-limiting examples of mating features include grooves, notches, ledges, and ridges. For example, the suture ring segments 807 shown in FIG. 8B includes mating feature 809, which in this instance is formed as a ledge along at least a portion of the length of the segment 807. In this instance, the mating feature 809 allows for a portion of the surface 813 of the leaflet 812 to "rest" on the suture ring segment 805 without having to be directly attached to it. The spring rib 818 is directly attached to the suture ring segment 807. In some instances, the spring rib 818 may be attached to a top portion of the suture ring segment 807. According to some embodiments, the mating feature may form the inner portion of the suture ring segment that is attached to elements of the leaflet subassembly, e.g., spring rib or leaflet.

The example configuration of FIGS. 8A and 8B is shown without the inclusion of a shielding structure, but it is to be appreciated that a shielding structure may be included according to other embodiments. For instance, the shielding structure may be attached to the segments of the suture ring, and the leaflets may attach to the shielding structure in a similar manner as described above. One example of a shielding structure attached to the valve assembly shown in FIGS. 8A and 8B is shown below in FIGS. 9A and 9B.

Figure 9A:
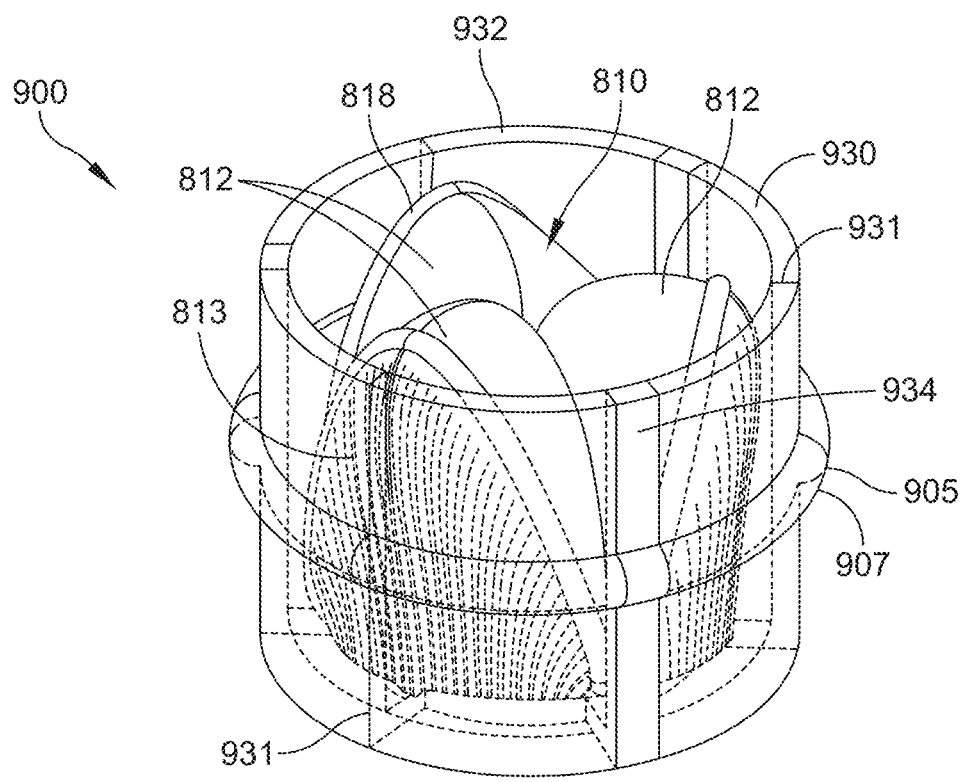
FIG. 9A is a perspective view of one example of a valve assembly that includes the leaflet subassembly of FIG. 8A with an example of a shielding structure and suture ring in an unexpanded configuration in accordance with one or more aspects of the invention.
Figure 9B:
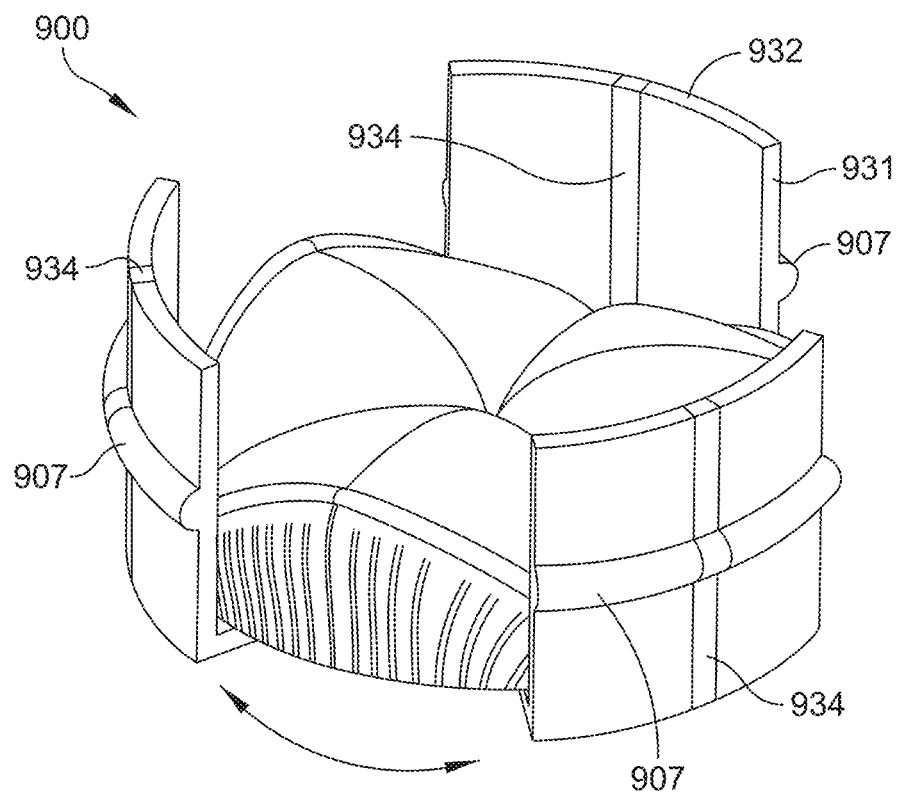
FIG. 9B is a perspective view of the leaflet subassembly, shielding structure, and suture ring of FIG. 9A in an expanded configuration.

Referring to FIGS. 9A and 9B, the leaflet subassembly 810 of FIGS. 8A and 8B is shown with one example of a shielding structure 930 and a suture ring 905 to form a valve assembly 900 in accordance with aspects of the disclosure. The shielding structure 930 includes shielding segments 932 that are positioned in between the leaflet subassembly 810 and the suture ring 905. In this example, the shielding structure 930 includes three shielding segments 932. An edge of a shielding segment is shown at 931. For purposes of illustration, shielding segments 932 of FIG. 9A are partially transparent to show portions of the underlying leaflet subassembly 810.

The shielding structure 930 also includes one or more shielding ribs 934. According to the example shown in FIGS. 9A and 9B, the shielding structure 930 includes three shielding ribs 934. Each of the shielding ribs 934 is configured to be positioned in the middle portion or center of the length of the shielding segment 932, i.e., the dimension that extends along the circumference of the suture ring 905. In some embodiments, the shielding rib 934 also extends through a portion of the suture ring segment 907, as shown in FIGS. 9A and 9B. The suture ring segments 907 therefore include or otherwise integrate a portion of the shielding rib 934. In other embodiments, the shielding rib 934 is not integrated with the suture ring segment 907. The suture ring segments 907 are configured to be attached to the annulus, as described above and therefore the suture ring 905 will expand radially outward to accommodate the growth of the annulus. Instead of the spring ribs 818 of the leaflet subassembly 810 attaching to the suture ring segments 807, as shown in FIGS. 8A and 8B, the spring ribs 818 are attached to the shielding rib 934, as described in further detail below in reference to FIGS. 9C and 9D. In addition, instead of the suture ring 805 being positioned at a lower portion of the leaflet subassembly 810, as shown in FIGS. 8A and 8B, the embodiment shown in FIGS. 9A and 9B has the suture ring 907 positioned at a central portion of the leaflet subassembly 810. Centering the suture ring 905 near the center of the valve assembly may allow the device to be more symmetrically positioned within the annulus, i.e. the valve assembly projects an equal amount on both sides of the annulus.

The shielding rib 934 is constructed from a biocompatible material as described herein, but in this instance the material used to construct the shielding rib 934 is more rigid than the material used to construct the shielding segment 932. The shielding segments 932 may therefore be constructed from a more "flexible" material that allows them to conform to the shape and contours of the annulus. The shielding ribs 934 may therefore function to add structural stability and integrity to the shielding structure 930.

In the unexpanded configuration shown in FIG. 9A, the edge of the shielding segment 932 does not overlap the edge of the adjacent shielding segment, but according to other embodiments adjacent shielding segments may be configured to overlap. In the expanded configuration shown in FIG. 9B, the shielding segments 932 and corresponding shielding ribs 934 expand radially outward with the suture ring segments 907 and with the annulus. The shielding segments 932 and corresponding shielding ribs 934 function to protect the leaflet subassembly 810.

Figure 9C:
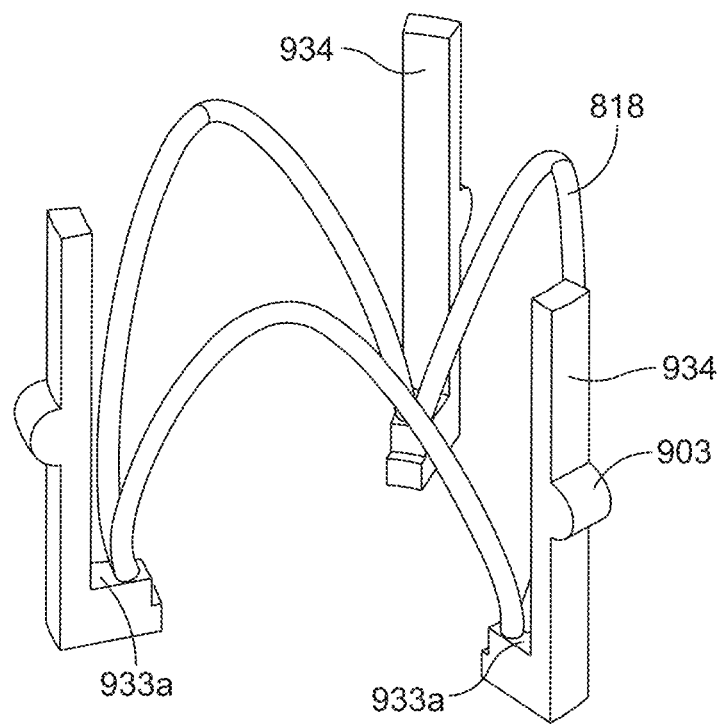
FIG. 9C is a perspective view of a portion of the leaflet subassembly and shield structure of FIG. 9A in an unexpanded configuration.

FIG. 9C is an unexpanded view of the shielding ribs 934 and spring ribs 818 of FIG. 9A. One or more portions of the suture ring segment may include a rigid portion 903, as shown in FIG. 9C. The rigid portion 903 of the suture ring segment according to this example is configured to be part of the shielding rib 934. As shown, the rigid portion 903 is dimensioned or otherwise configured to integrate with the other non-rigid portions of the suture ring segment 907 (e.g., see FIG. 9B). In this example, the suture ring segment 907 is at least partially integrated with the shielding segment 932 and shielding rib 934. For example, each shielding segment 932, shielding rib 934, and suture ring segment 907 may form a continuous structure, as shown in FIG. 9B. In a similar manner as with the shielding segment 932, the rigid portion 903 may also be positioned in the middle portion or center of the length of the suture ring segment 907.

Figure 9D:
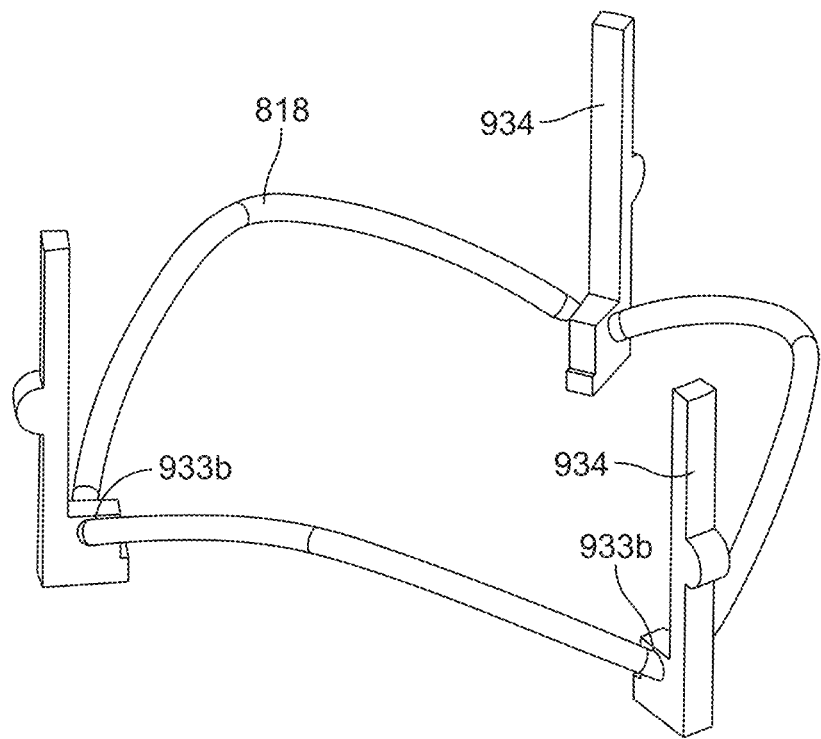
FIG. 9D is a perspective view of a portion of the leaflet subassembly and shield structure of FIG. 9C in an expanded configuration.

As shown, the spring ribs 818 of the leaflet subassembly are attached to the shielding ribs 934 such that one end of the shielding rib is attached to a first shielding rib and the other end of the shielding rib is attached to a second shielding rib that is adjacent to the first shielding rib. One end of two adjacent spring ribs 818 are therefore attached to each shielding rib 934. The spring ribs 818 and shielding ribs 934 may therefore form a "skeleton" or frame for the valve assembly. The spring rib 818 of FIG. 9C is attached to an attachment feature 933a, which in this instance is the top portion of a "ledge" extending from the bottom portion (i.e., downstream side) of the shielding rib 934. The spring rib 818 may be attached to the shielding rib 934 using any one of a number of different mechanisms, including direct bonding between the two mating surfaces, or by using apertures in the shielding rib 934. For instance, end portions of the spring ribs 818 may be positioned into apertures or holes in the shielding rib 934. The expanded configuration shown in FIG. 9D shows a different location for the attachment feature, shown as 933b, and is shown as two apertures placed in side surfaces of the ledge of the shielding rib 934. The end portions of two adjacent spring ribs 818 can therefore be positioned in these apertures, as shown. According to other embodiments, the spring ribs 818 and shielding ribs 934 may be integrated together to form a continuous structure, i.e., a single piece. In this instance, the spring ribs 818 may be constructed from a different material than the shielding ribs 934, but still form a continuous structure with the shielding ribs 934. Other components of the valve assembly may also be integrated together with the spring ribs 818 and shielding ribs 934 to from a continuous structure, including the shielding segments 932, suture ring segments 907, and/or leaflets 812.

Figure 9E:
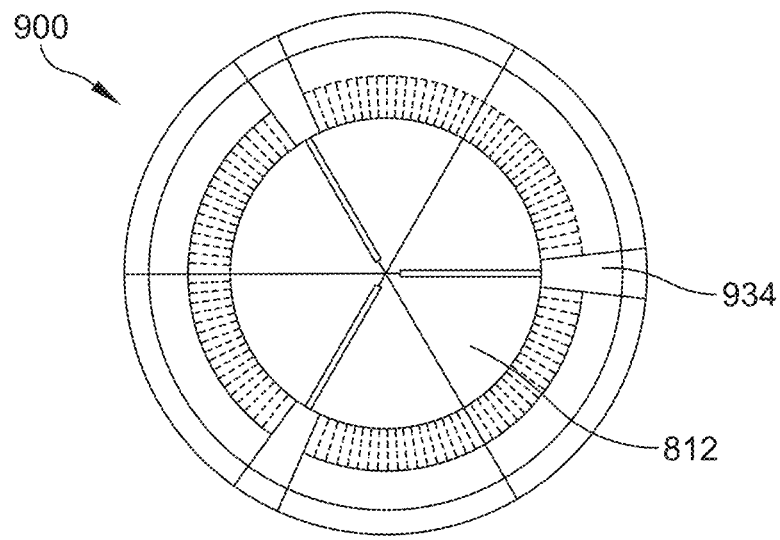
FIG. 9E is a plan view of the downstream side of the valve assembly of FIG. 9A in an unexpanded configuration.
Figure 9F:
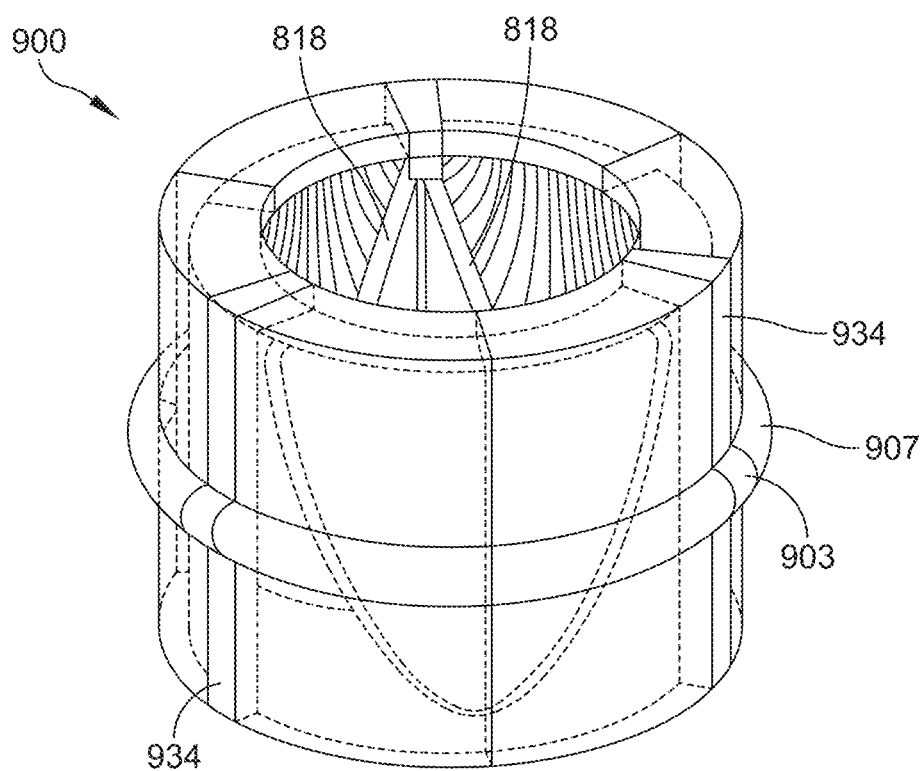
FIG. 9F is a perspective view of the downstream side of the valve assembly of FIG. 9A in an unexpanded configuration.
Figure 9G:
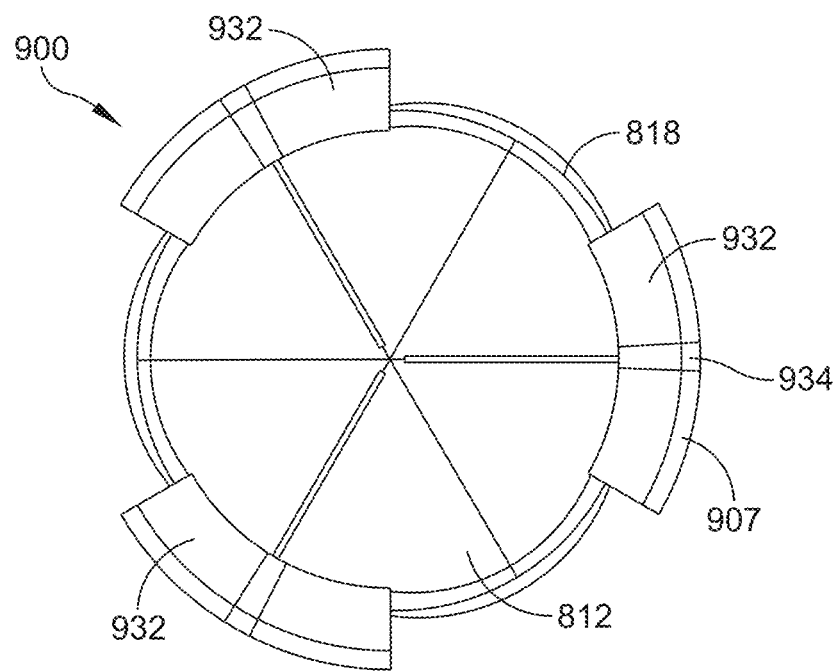
FIG. 9G is a plan view of the downstream side of the valve assembly of FIG. 9A in an expanded configuration.
Figure 9H:
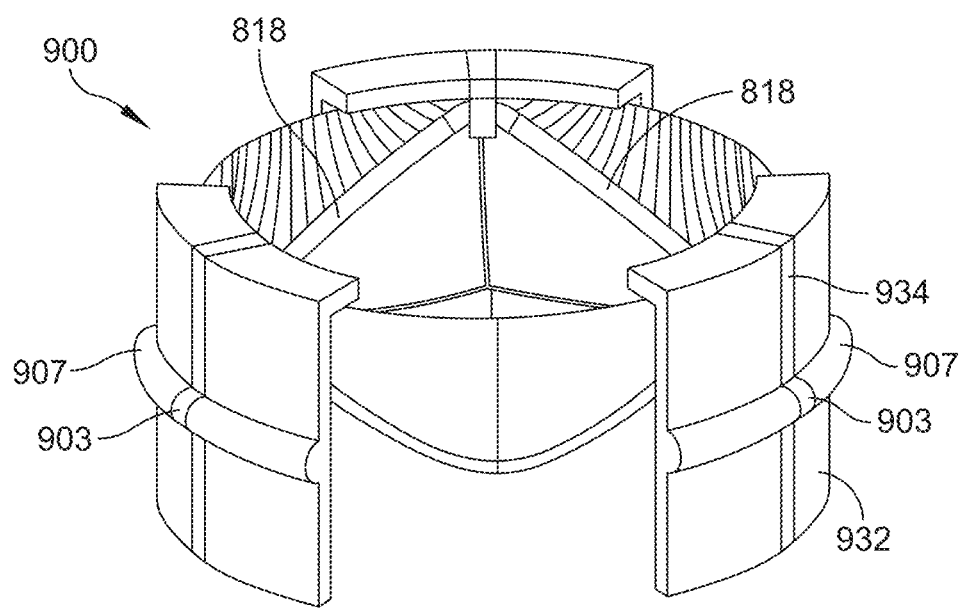
FIG. 9H is a perspective view of the downstream side of the valve assembly of FIG. 9A in an expanded configuration.

FIGS. 9E-9H are additional views of the valve assembly 900 of FIG. 9A, with FIGS. 9E and 9F showing plan and perspective views, respectively, of the downstream side of the valve assembly 900 in an unexpanded configuration, and FIGS. 9G and 9H showing plan and perspective views, respectively, of the downstream side of the valve assembly 900 in an expanded configuration. As discussed above in reference to FIGS. 8A and 8B, the spring ribs 818 are compressed in the unexpanded state (e.g., FIGS. 9E and 9F) and release the stored compressive energy as the device expands to the expanded state, where the spring ribs 818 have expended the compressive energy and are in a relaxed state.

Figure 10:
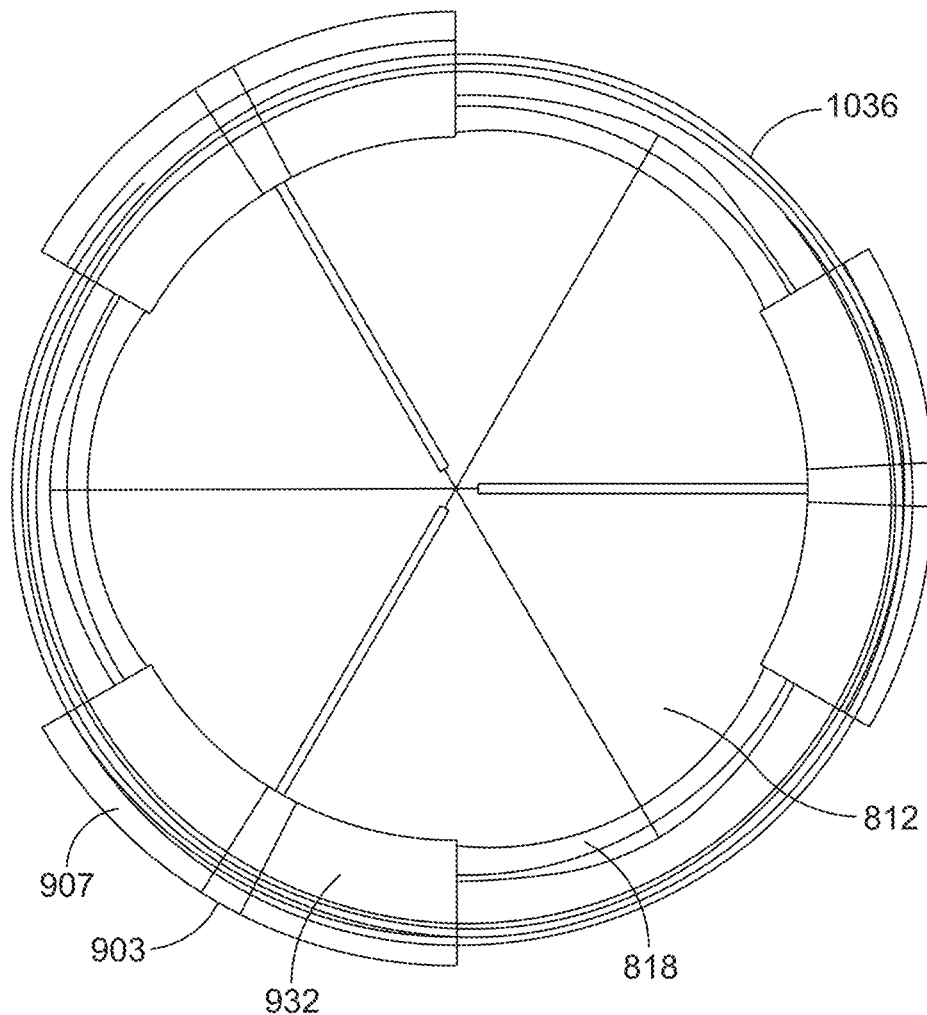
FIG. 10 is a plan view of the downstream side of the valve assembly of FIG. 9A in an expanded configuration with one example of a shielding structure in accordance with one or more aspects of the invention.

According to some embodiments, the shielding structure further includes a coiled member that is at least partially integrated with the shielding segments. An example of a coiled member is shown in FIG. 10 as coiled member 1036, which in this example is a spiral coiled biocompatible metal or metal alloy that is integrated with each of the shielding segments 932. FIG. 10 is a plan view of the downstream side of the valve assembly 900 of FIG. 9A in the expanded configuration (i.e., FIG. 9G with the inclusion of the coiled member 1036). For purposes of illustration, the shielding segments 932 and shielding ribs 934 are shown to be at least partially transparent to reveal the contained coiled member 1036. The example shown in FIG. 10 shows the coiled member 1036 in an expanded state. When the valve assembly is in an unexpanded state, the coiled member 1036 is also in an unexpanded state and is configured to store expansive energy that is released as the device expands with the annulus. The coiled member 1036 may be shaped as a tubular or cylindrical shape where the diameter of the tube or cylinder increases as the coiled member 1036 radially expands outward with the valve assembly. In some instances, the coiled member is configured to not increase in length as it expands radially outward.

The coiled member 1036 may be integrated with the shielding segment 932 such that it extends through the entirety of the length of the shielding segment 932, including the shielding rib 934 and portions of the height of the shielding segment 932 (and shielding rib 934). As the valve assembly expands, the coiled member 1036 covers the gaps in between the shielding segments 932, as shown in FIG. 10.

Figure 11A:
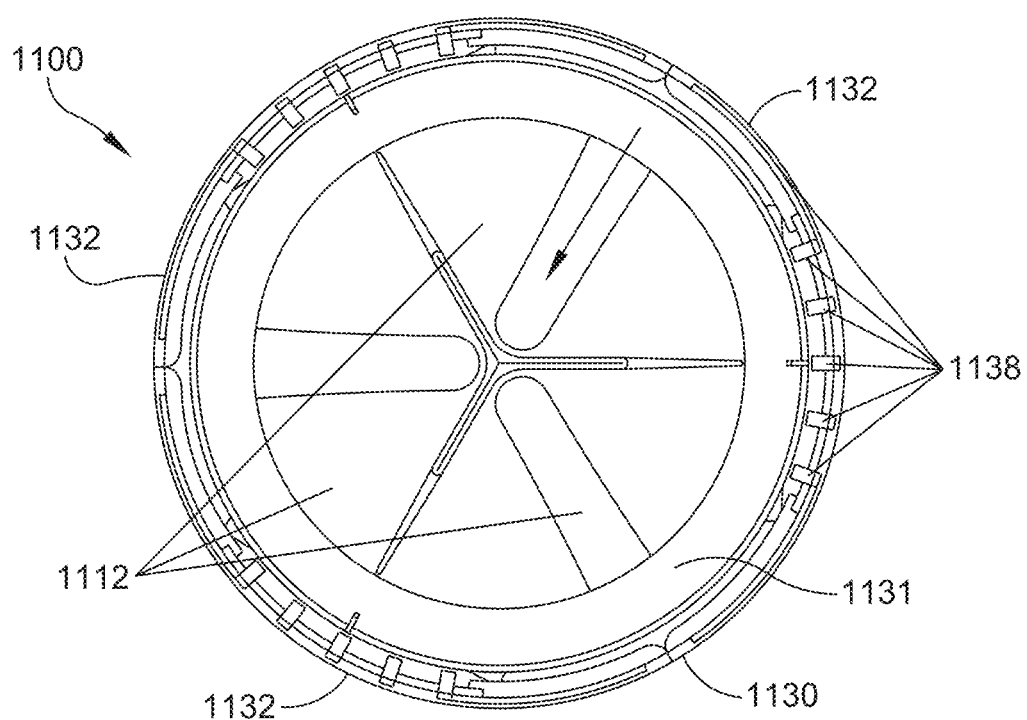
FIG. 11A is a plan view of the downstream side of another example of a valve assembly in an expanded configuration in accordance with one or more aspects of the invention.
Figure 11B:
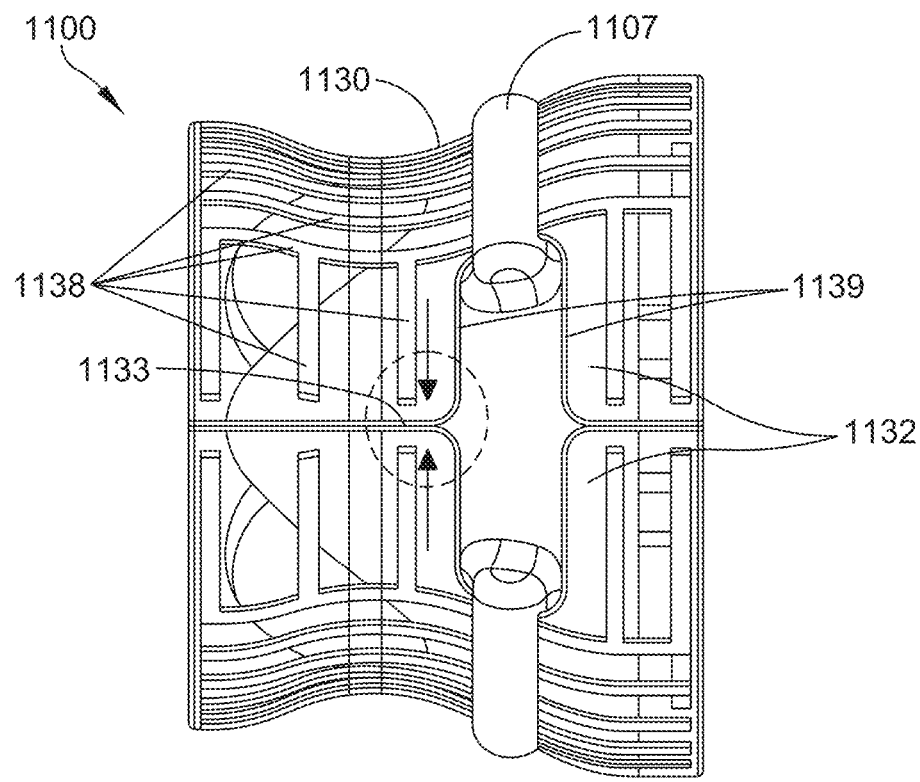
FIG. 11B is a side view of the valve assembly shown in FIG. 11A.
Figure 11C:
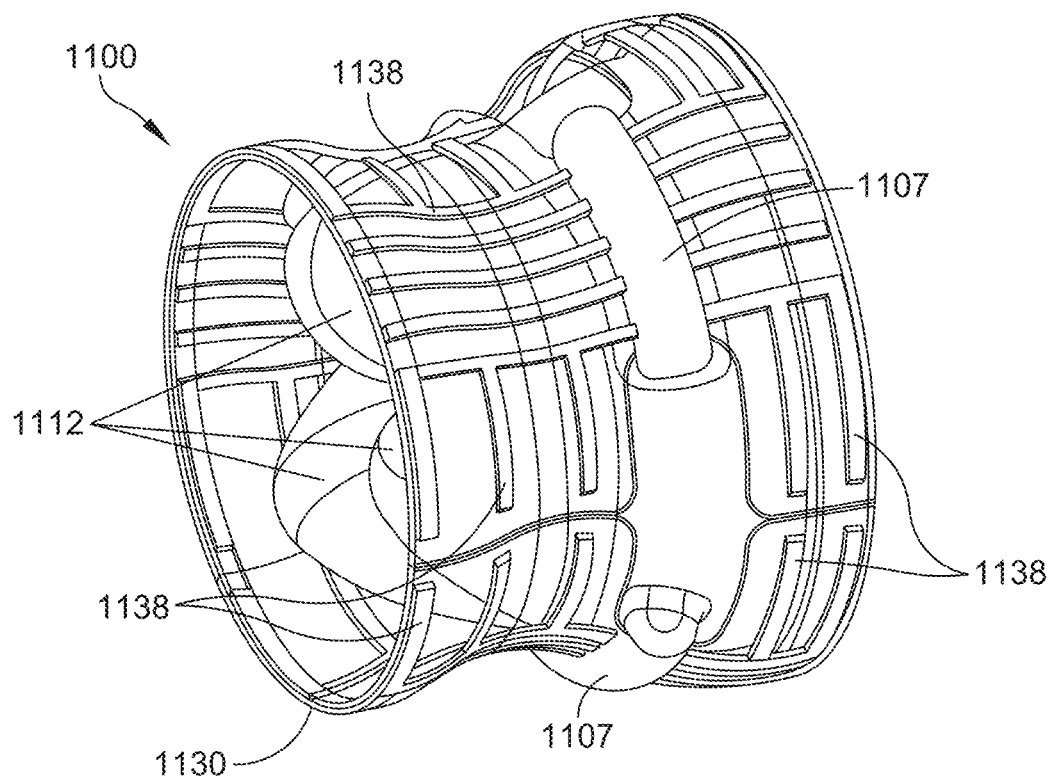
FIG. 11C is a perspective view of the upstream side of the valve assembly of FIG. 11A.
Figure 11D:
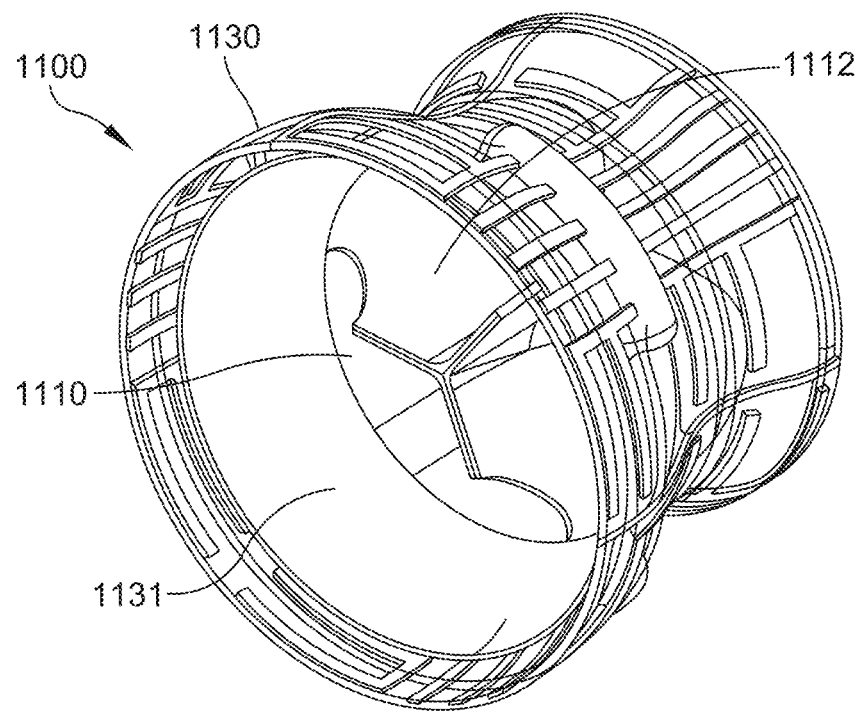
FIG. 11D is a perspective view of the downstream side of the valve assembly of FIG. 11A.

Referring now to FIGS. 11A-11D, another example of a valve assembly 1100 is shown in an expanded configuration. FIG. 11A is a plan view of the downstream side of the valve assembly 1100, FIG. 11B is a side view, FIG. 11C is a perspective view of the upstream side, and FIG. 11D is a perspective view of the downstream side.

According to at least one embodiment, the shielding structure is internally reinforced or otherwise supported with a reinforcing material. According to various aspects, the reinforcement material may be arranged in a pattern to provide axial and circumferential stiffness or support to the shielding structure. An example of an internally reinforced shielding structure is shown in the valve assembly 1100 of FIGS. 11A-11D. According to this example, the valve assembly 1100 includes three suture ring segments 1107, which are attached or otherwise coupled to a leaflet subassembly 1110 that includes three leaflets 1112 and a shielding structure 1130 that includes three shielding segments 1132. In FIG. 11B, two shielding segments 1132 meet at edge 1133. For purposes of illustration, the shielding segments 1132 of FIGS. 11B-11D are shown to be at least partially transparent to reveal the underlying structures. Each of the shielding segments 1132 includes reinforcement material 1138. The reinforcement material 1138 may be a biocompatible material that is more rigid than the material used to form the main body of the shielding segment 1132. In some embodiments, both the reinforcement material 1138 and the main body of the shielding segment 1132 are made from different polymers. For instance, the reinforcement material 1138 may be a metal alloy, such as nitinol or platinum-iridium materials, whereas the shielding segment 1132 may be formed from a polymer. The reinforcement material 1138 may be "woven" or otherwise integrated into the material of the shielding segment 1132. In some embodiments, the reinforcement material 1138 may be woven as a geometric or non-geometric pattern into the shielding segment 1132. The reinforcement material 1132 may be arranged in rows, lines, a geometric pattern, or any other geometric arrangement. In some embodiments, the reinforcement material 1138 may be arranged in a pattern for purposes of tuning the axial and circumferential stiffness of the shielding structure 1130. For instance, the pattern can be configured to allow the axial stiffness to be larger than the circumferential stiffness, which allows the radius of curvature of the shielding structure 1130 to adapt to the growth of the annulus.

In the unexpanded configuration, portions of adjacent shielding segments 1132 are configured to overlap, and as the device expands, adjacent shielding segments 1132 abut one another (see FIG. 11B) such that the shielding structure forms a continuous external surface around at least a portion of the circumference of the valve assembly. In addition, the shielding segments 1132 include alignment features 1139, which function in a similar manner as the alignment features 639 described above in reference to FIG. 6.

As best shown in FIGS. 11A and 11D, the shielding structure 1130 also includes a sealing member 1131 positioned on the downstream side of the valve assembly 1100. The sealing member 1131 may attach to one or more portions of the leaflet subassembly 1110, such as the leaflets themselves. In some instances, the sealing member 1131 may be constructed as a "flap" that extends from the leaflet subassembly 1110. The sealing member 1131 is also positioned or integrated with an interior portion of the shielding segments and may form a continuous surface around the inner circumference of the valve assembly. The sealing member 1131 may function to aid in "sealing" the leaflets 1112. For instance, the sealing member 1131 may aid in isolating the leaflets 1112 from other portions of the shielding structure 1130, such as the edges of the individual shielding segments 1132 which may have gaps or seams that could allow fluid to leak through (e.g., see circled region in FIG. 11B). The sealing member 1131 may therefore function to mitigate regurgitation of fluid at these edges of the shielding segments 1132. In the unexpanded configuration, the downstream edge of the sealing member 1131 is configured to fold inward, as indicated by the arrow shown in FIG. 11A.

Figure 12A:
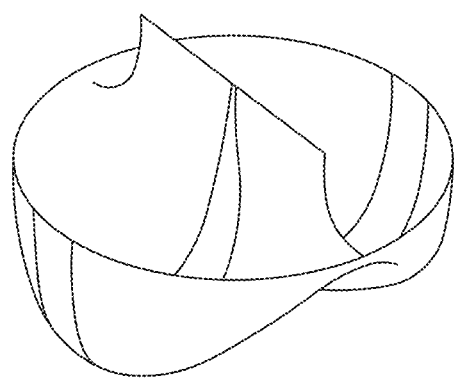
FIGS. 12A-12X are perspective views of the downstream side of multiple examples of leaflet subassemblies in accordance with one or more aspects of the invention.
Figure 12B:
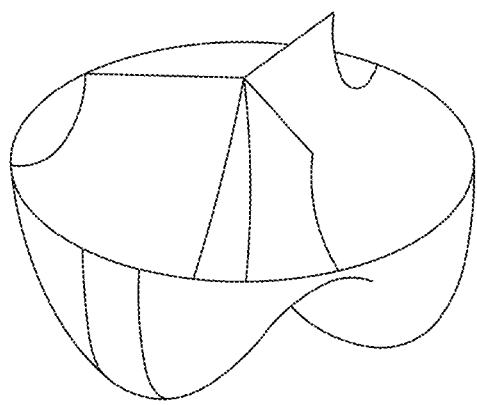
Figure 12C:
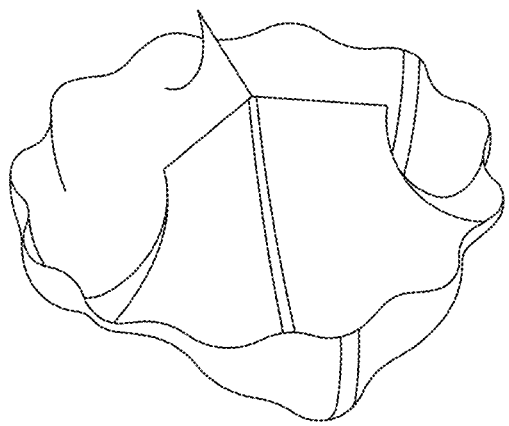
Figure 12D:
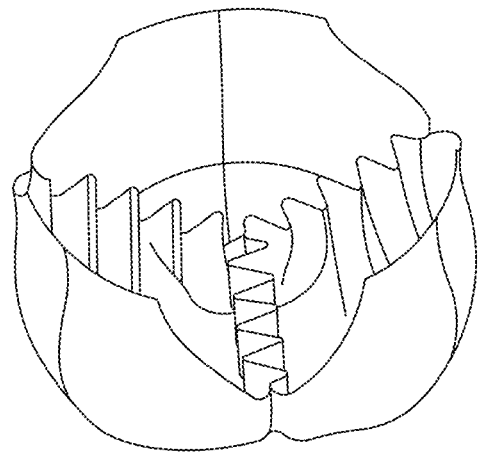
Figure 12E:
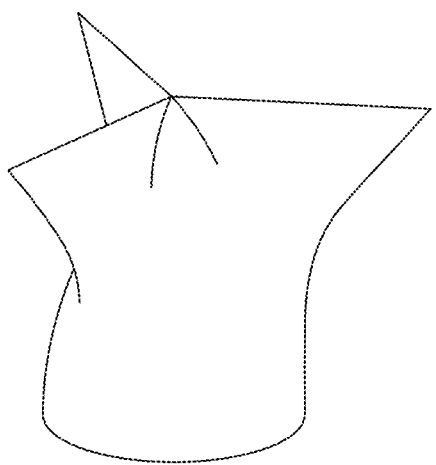
Figure 12F:
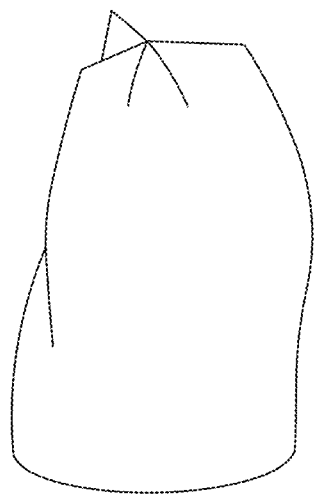
Figure 12G:
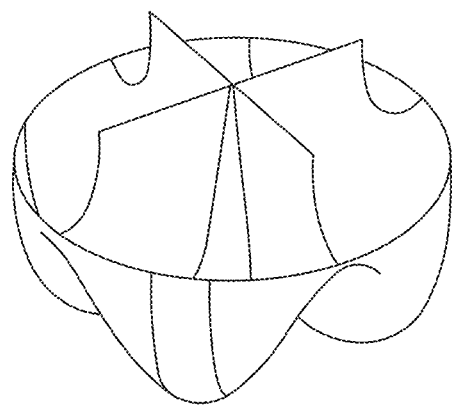
Figure 12H:
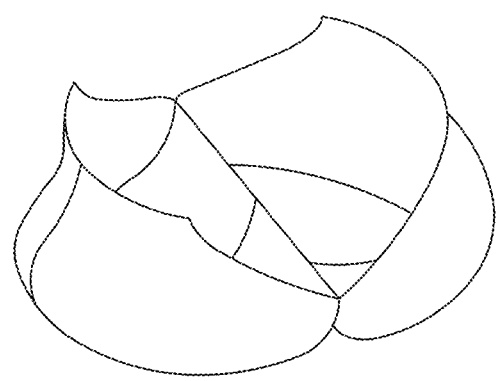
Figure 12I:
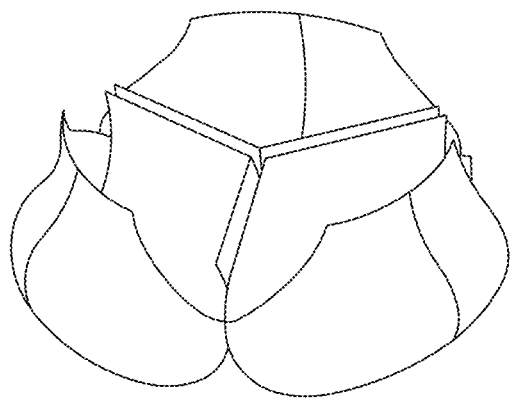
Figure 12J:
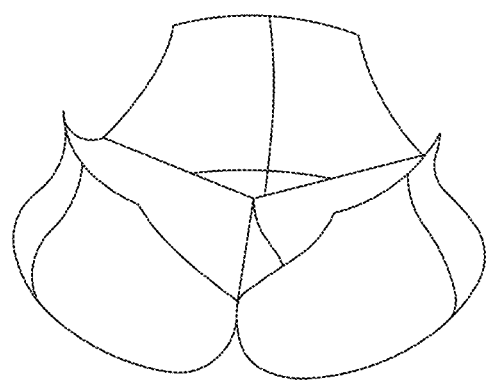
Figure 12K:
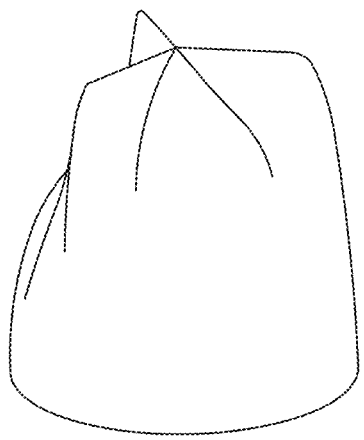
Figure 12L:
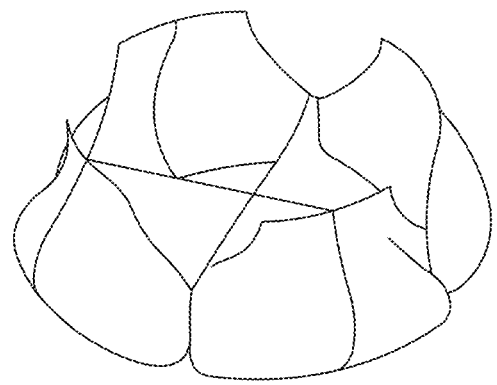
Figure 12M:
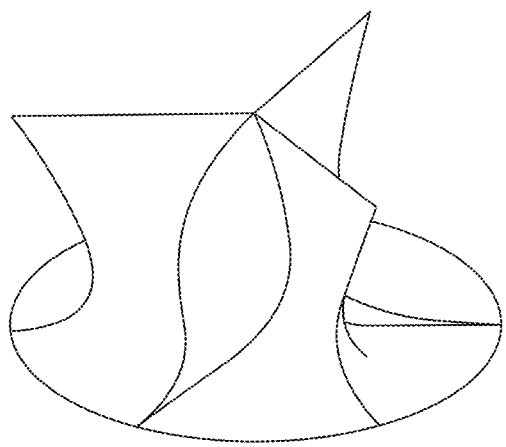
Figure 12N:
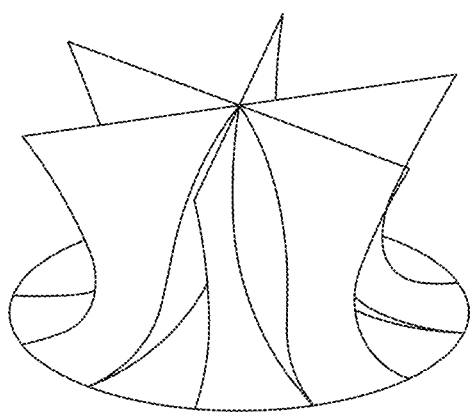
Figure 12O:
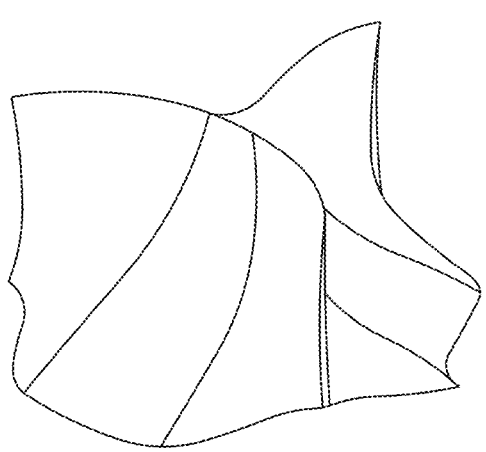
Figure 12P:
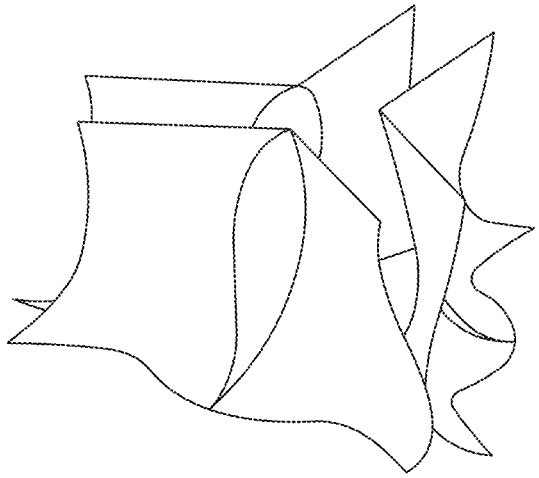
Figure 12Q:
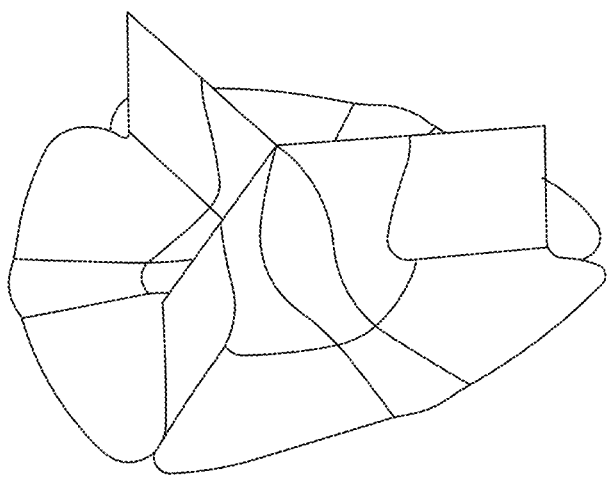
Figure 12R:
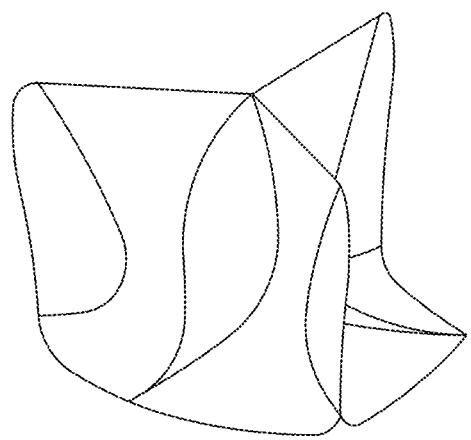
Figure 12S:
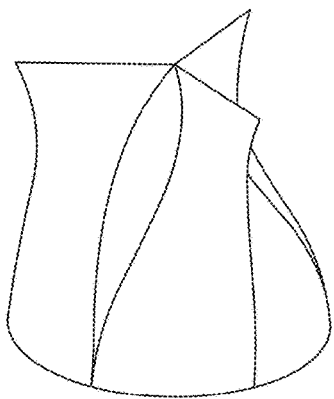
Figure 12T:
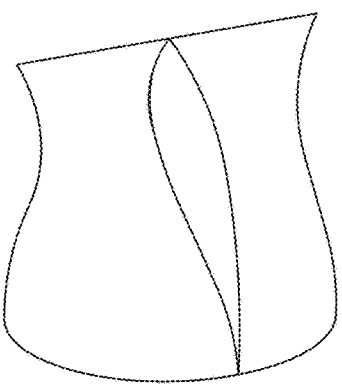
Figure 12U:
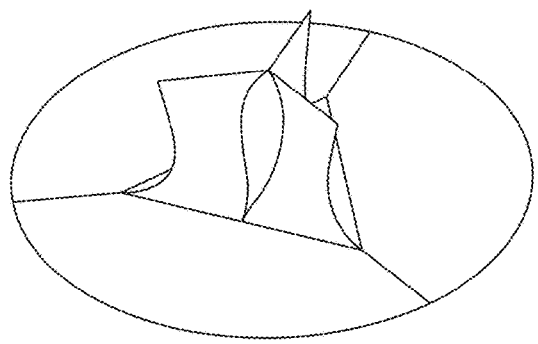
Figure 12V:
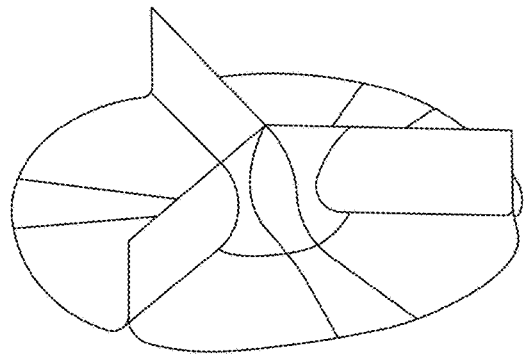
Figure 12W:
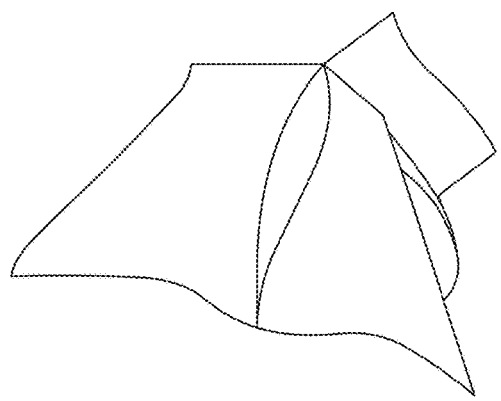
Figure 12X:
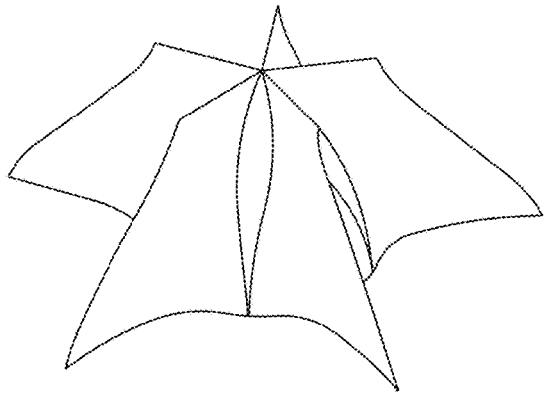

FIGS. 12A-12X show the downstream side of examples of various leaflet subassemblies in accordance with aspects of the disclosure. The leaflet topologies shown in FIGS. 12A-12X include two, three, four, and six leaflet geometries that may be suitable for use in one or more of the embodiments of the valve assemblies discussed above. In addition, one or more features of the individual leaflet subassemblies shown in FIGS. 12A-12X may be recombined with other leaflet subassemblies.

One or more of the leaflet subassemblies shown in FIGS. 12A-12X may be configured to provide one or more advantages to the valve assembly, including low turbulent intensity to the fluid as it flows through the device, and/or inhibiting platelet activation. Other advantages that may be provided by one or more of the examples shown in FIGS. 12A-12X include the ability to produce low shear and turbulent stresses in the fluid passing through the valve assembly, as well as having low thrombogenicity. Some of the designs may also have features that mimic a native valve arrangement.

The valve assemblies discussed herein offer several advantages over typical prosthetic valve devices. For instance, typical prosthetic valve devices include continuous suture rings that are incapable of expansion and therefore cannot be used in growing patients. The segmented construction offered by the suture rings (and in some embodiments the shielding structures) discussed herein allow for the valve assembly to expand with the patient. In addition, the geometries used in typical valve replacement devices are designed to be similar to native valves and cannot accommodate expansion. The leaflet subassemblies disclosed herein are capable of enabling valve function over a range of annulus diameters with a single surgery and device. Furthermore, valve assemblies that are individually modified by physicians for use in smaller patients, e.g., pediatric patients, are costly due to the high scrap rate and skilled labor used in their construction and also provide limited expansion ratios and ranges of expansion. This leads to multiple surgeries as the patient grows, and poor resistance to foreign object damage, such as those caused by catheters (e.g., used to expand the device). The disclosed valve assemblies are capable of expanding passively as the tissue to which they are attached grows. In addition, the disclosed valve assemblies can be implemented at arbitrary diameters, provide larger expansion ratios, require few or no modification operations done by hand, and in some instances may also not require harvesting of xenograft or homograft tissue. Thus, fewer surgical interventions are required during the life of the patient since the disclosed devices can accommodate a wider range of patients (ages and sizes) for a longer period of time at a potentially lower cost.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. A segmented, growth-accommodating prosthetic valve assembly for controlling fluid flow in an annulus, the prosthetic valve assembly comprising:

a suture ring formed from two or more separate segments, each segment of the two or more separate segments having an outer portion configured for attachment to the annulus, the suture ring being circumferentially discontinuous including a gap between adjacent segments of the two or more separate segments, the suture ring conforming to the annulus while being passively expandable, due to a restoring spring force provided by the segments of the suture ring, from an initial radially-unexpanded implanted diameter to a final expanded diameter in which the two or more separate segments are spaced further apart from each other than in the initial radially-unexpanded implanted diameter, to accommodate growth of the annulus, an expansion ratio of an outer diameter of the suture ring between the initial radially-unexpanded implanted diameter and the final expanded diameter being about 1.5 to about 5; and a leaflet subassembly attached to an inner portion of at least one segment of the two or more segments of the suture ring, the leaflet subassembly including at least one leaflet configured for controlling a flow of fluid through the prosthetic valve assembly.

2. The prosthetic valve assembly of claim 1, wherein the at least one leaflet includes an outer edge configured to attach to the inner portion of the at least one segment.

3. The prosthetic valve assembly of claim 2, wherein the at least one leaflet and the at least one segment form a continuous structure.

4. The prosthetic valve assembly of claim 2, wherein the leaflet subassembly further includes a spring rib coupled to the at least one leaflet.

5. The prosthetic valve assembly of claim 4, wherein a portion of the spring rib is attached to the inner portion of the at least one segment.

6. The prosthetic valve assembly of claim 4, wherein a surface of the at least one leaflet has a plurality of expansion elements.

7. The prosthetic valve assembly of claim 6, wherein the plurality of expansion elements are pleats.

8. The prosthetic valve assembly of claim 1, further comprising a shielding structure attached to the suture ring and configured to extend laterally between the at least one leaflet and the annulus, the shielding structure defined by a plurality of shielding segments.

9. The prosthetic valve assembly of claim 8, wherein the leaflet subassembly includes a sinus structure.

10. The prosthetic valve assembly of claim 8, wherein the shielding segments are more rigid than the at least one leaflet.

11. The prosthetic valve assembly of claim 8, wherein at least a portion of each shielding segment of the plurality of shielding segments is attached to a segment of the two or more segments of the suture ring.

12. The prosthetic valve assembly of claim 8, wherein the suture ring, the at least one leaflet, and the shielding structure form a continuous structure.

13. The prosthetic valve assembly of claim 8, wherein a portion of a shielding segment of the plurality of shielding segments is coupled to an adjacent shielding segment of the plurality of shielding segments.

14. The prosthetic valve assembly of claim 13, wherein the adjacent shielding segments are coupled with a ligament.

15. The prosthetic valve assembly of claim 8, wherein at least a portion of at least one shielding segment of the plurality of shielding segments overlies at least a portion of at least one adjacent shielding segment of the plurality of shielding segments when the prosthetic valve assembly is in a radially-unexpanded configuration.

16. The prosthetic valve assembly of claim 15, wherein the at least one shielding segment does not overlap the at least one adjacent shielding segment when the prosthetic valve assembly is in the radially-expanded configuration.

17. The prosthetic valve assembly of claim 8, wherein the shielding structure further includes a plurality of shielding ribs.

18. The prosthetic valve assembly of claim 17, wherein the plurality of shielding ribs are more rigid than the plurality of shielding segments.

19. The prosthetic valve assembly of claim 17, wherein the plurality of shielding ribs extend along a height of the shielding structure.

20. The prosthetic valve assembly of claim 8, wherein the shielding structure further includes a coiled member that is at least partially integrated with the plurality of shielding segments.

21. The prosthetic valve assembly of claim 8, wherein the shielding structure is supported with a reinforcing material.

22. The prosthetic valve assembly of claim 21, wherein the reinforcing material is arranged in a pattern to provide axial and circumferential support to the shielding structure.

23. The prosthetic valve assembly of claim 1, wherein the at least one leaflet includes a plurality of leaflets.

24. The prosthetic valve assembly of claim 23, wherein the plurality of leaflets are asymmetrically disposed about a central longitudinal axis of the prosthetic valve assembly.

25. The prosthetic valve assembly of claim 23, wherein each leaflet of the plurality of leaflets has a free edge that is flared.

26. The prosthetic valve assembly of claim 23, wherein each leaflet of the plurality of leaflets has an uncoupled mating edge positioned adjacent an uncoupled mating edge of an adjacent leaflet.

27. The prosthetic valve assembly of claim 23, wherein the plurality of leaflets remain in contact with each other as the suture ring expands from the initial radially-unexpanded implanted diameter to the final expanded diameter to accommodate growth of the annulus.

28. The prosthetic valve assembly of claim 1, configured to accommodate annulus diameters ranging from about 5 millimeters to about 40 millimeters.

* * * * *